United States Patent
Watanabe et al.

(10) Patent No.: US 7,569,730 B2
(45) Date of Patent: Aug. 4, 2009

(54) BISPHOSPHINE LIGAND

(75) Inventors: Michimasa Watanabe, Toyama (JP); Yuhki Takeuchi, Toyama (JP); Takahiro Isobe, Toyama (JP); Tadashi Takeuchi, Toyama (JP)

(73) Assignee: Daiichi Fine Chemical Co., Ltd., Toyama (JP)

( * ) Notice: Subject to any disclaimer, the term of this patent is extended or adjusted under 35 U.S.C. 154(b) by 0 days.

(21) Appl. No.: 12/054,917

(22) Filed: Mar. 25, 2008

(65) Prior Publication Data

US 2008/0242534 A1 Oct. 2, 2008

(30) Foreign Application Priority Data

Mar. 26, 2007 (JP) ............................. 2007-078384

(51) Int. Cl.
C07F 9/02 (2006.01)
B01J 23/40 (2006.01)
(52) U.S. Cl. .......................................... 568/8; 502/326
(58) Field of Classification Search .................... 568/8; 502/326
See application file for complete search history.

(56) References Cited

U.S. PATENT DOCUMENTS

2005/0288523 A1 12/2005 Knochel et al.

FOREIGN PATENT DOCUMENTS

| EP | 1 595 885 A2 | 11/2005 |
|---|---|---|
| JP | 2005-336181 | 12/2005 |
| WO | 91/17998 | 11/1991 |
| WO | 93/01199 | 1/1993 |

OTHER PUBLICATIONS

English Language Abstract of JP 2005-336181 (provided by Esp@cenet).
Catalytic Asymmetric Synthesis, Second Edition, Ed., Iwao Ojima, Wiley-VCH, pp. v-vii, ix-xiv, 1, and 797-99 (2000).
Inoguchi et al., "Development of a New Six-Membered Chelating Chiral [Bisphosphine]rhodium Catalyst and Efficient Asymmetric Hydrogenation of (Z)-2-Acetamidocinnamic Acid" *SYNLETT* 49-51 (1991).
Corey et al., "Stereo-Controlled Synthesis of Prostaglandins $F_{2\alpha}$ and $E_2$ (*dl*)" *J. Am. Chem. Soc.*, vol. 91, No. 20, pp. 5675-5677 (1969).
"Organic Metal Complex" Jikken Kagaku Koza (Lecture of Experimental Chemistry), 4th edition, edited by the Chemical Society of Japan, vol. 18, pp. 338-345 (1991) Maruzen, along with a partial English language translation.
M. Kitamura, *Org. Synth.*, vol. 71, pp. 1-13 (1993).
F. Sato, Gosei Kagakusha no tameno Jikken Yuki Kinzoku Kagaku (Experimental Organic Metal Chemistry for Synthetic Chemists), pp. 195-196, Kodansha (1992), along with a partial English language translation.
"Organic Metal Complex" Jikken Kagaku Koza (Lecture of Experimental Chemistry), 4th edition, edited by the Chemical Society of Japan, vol. 18, p. 362-364 (1991), along with a partial English language translation.

*Primary Examiner*—Jafar Parsa
(74) *Attorney, Agent, or Firm*—Greenblum and Bernstein P.L.C.

(57) ABSTRACT

A compound represented by the following general formula (I):

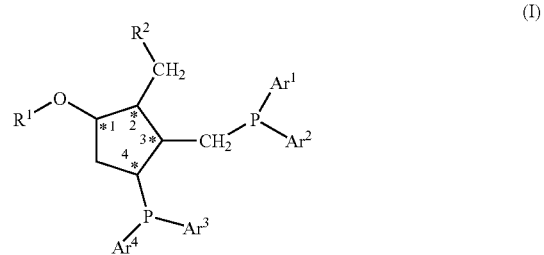

(I)

[wherein $R^1$ represents hydrogen atom, or an alkyl group, $R^2$ represents a hydroxyalkyl group, or a triarylmethyloxyalkyl group, or $R^1$ and $R^2$ combine together to represent —C($R^3$)($R^4$)— ($R^3$ and $R^4$ represent hydrogen atom, an alkyl group, or hydroxyl group, or $R^3$ and $R^4$ may combine together to represent oxo group), or —C($R^5$)($R^6$)—O—C($R^7$)($R^8$)— ($R^5$ to $R^8$ represent hydrogen atom, an alkyl group, or hydroxyl group, or $R^5$ and $R^6$ may combine together to represent oxo group, and $R^7$ and $R^8$ may combine together to represent oxo group); $Ar^1$ to $Ar^4$ independently represent an aryl group (the aryl group may have 1 to 5 of the same or different substituents), *1 to *4 indicate asymmetric carbons, and configurations are cis between *1 and *2, cis between *3 and *4, and trans between *2 and *3]. An optically active phosphine ligand which can be easily synthesized and gives a transition metal complex showing superior asymmetric catalyst activity is provided.

13 Claims, No Drawings

BISPHOSPHINE LIGAND

TECHNICAL FIELD

The present invention relates to a novel bisphosphine ligand having a cyclopentane structure and a novel catalyst comprising the ligand and a transition metal, and also to use of the catalyst.

BACKGROUND ART

Many agents such as medicaments and agricultural chemicals utilizing an optically active compound as an active ingredient are known. A number of methods are known as methods for preparing optically active compounds. Among them, the catalytic asymmetric synthesis technique is one of extremely powerful means. Since transition metal complexes having optically active phosphine as a ligand have superior catalytic activity and stereoselectivity for the catalytic asymmetric synthesis, they are also applied to industrial manufacturing processes (CATALYTIC ASYMMETRIC SYNTHESIS, Ed., Iwao Ojima, Wiley-VCH, 2000).

As optically active ligands which can form asymmetric catalysts, phosphine ligands and phosphorane ligands are known. As the phosphine ligands, for example, BPPM, BINAP, DIOP and the like are known, and as the phosphorane ligands, DuPHOS, BPE and the like are known. Although many of the phosphine ligands except for BINAP can be used for asymmetric hydrogenation of acetamidoacrylates, many of the ligands have rather narrower applicable range for other substrates. Moreover, they have problems in industrial application, for example, the synthetic route is long and each enantiomer cannot be obtained easily. The phosphorane ligands are reported to have characteristics not possessed by the conventional phosphine ligands, and to be excellent asymmetric hydrogenation catalysts (WO93/01199 (DuPHOS), WO91/17998 (BPE)). However, in order to form a phosphorane ring, an expensive optically active 1,3- or 1,4-diol is needed, and in addition, Et-DuPHOS, Et-BPE, Me-BPE and the like are oily substances and therefore have problems of susceptibility to oxidization and difficulty in handling.

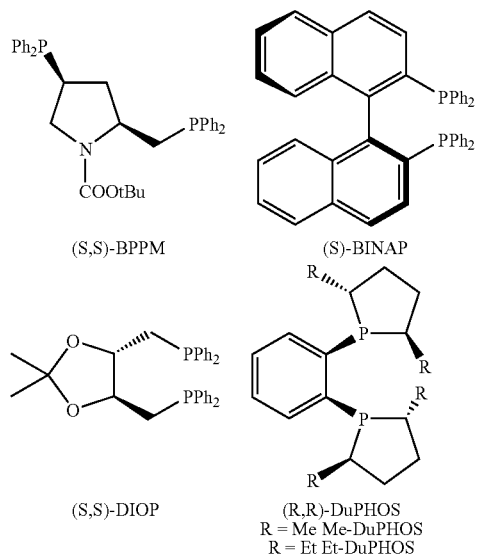

(S,S)-BPPM  (S)-BINAP (S,S)-DIOP  (R,R)-DuPHOS
R = Me Me-DuPHOS
R = Et Et-DuPHOS

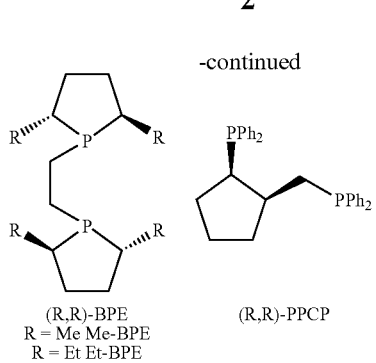

(R,R)-BPE  (R,R)-PPCP
R = Me Me-BPE
R = Et Et-BPE (In the formulas, Me represents methyl group, and Et represents ethyl group.)

It is reported by Achiwa et al. that the phosphine ligand, PPCP, having a cyclopentane structure and forming a 6-membered ring chelate is fixed in the Skew arrangement and has superior stereoselectivity (Synlett, 49, 1991). However, it is difficult to modify the cyclopentane structure in the synthetic route in which a beta-ketoester compound is asymmetrically reduced with BINAP-Ru, and the resultant ester is reduced with a hydride. It is not easy to design and use an suitable ligand depending on a given substrate.

Although a catalyst having a cyclopentane structure is also disclosed in Japanese Patent Unexamined Publication (Kokai) No. 2005-336181, the asymmetric hydrogenation reaction characteristic to the present invention is not described.

DISCLOSURE OF THE INVENTION

Object to be Achieved by the Invention

An object of the present invention is to provide an optically active phosphine ligand which can be easily synthesized and provides a transition metal complex superior in asymmetric catalyst activity. Another object of the present invention is to provide an optically active ligand which has a chemical structure easily synthesizable by choosing suitable substituents depending on a substrate, and either or both enantiomers of which ligand is readily synthesizable.

Means for Achieving the Object

The inventors of the present invention conducted various researches in order to achieve the foregoing objects. As a result, they found that the compounds represented by the following general formula (I) were easily synthesizable and had extremely superior features as a ligand for providing a transition metal complex superior in asymmetric catalyst activity, and accomplished the present invention.

The present invention thus provides a compound represented by the following general formula (I):

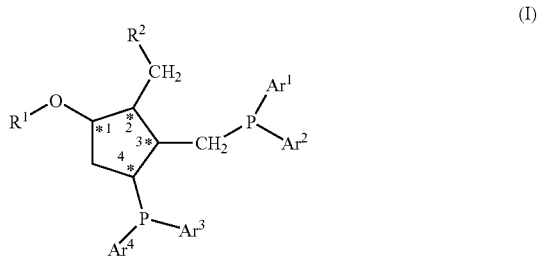

(I)

[wherein $R^1$ represents hydrogen atom, or an alkyl group, $R^2$ represents a hydroxyalkyl group, or a triarylmethyloxyalkyl group, or $R^1$ and $R^2$ combine together to represent —C($R^3$)($R^4$)— ($R^3$ and $R^4$ independently represent hydrogen atom, an alkyl group, or hydroxyl group, or $R^3$ and $R^4$ may combine together to represent oxo group), or —C($R^5$)($R^6$)—O—C($R^7$)($R^8$)— ($R^5$, $R^6$, $R^7$ and $R^8$ independently represent hydrogen atom, an alkyl group, or hydroxyl group, or $R^5$ and $R^6$ may combine together to represent oxo group, and/or $R^7$ and $R^8$ may combine together to represent oxo group); $Ar^1$, $Ar^2$, $Ar^3$ and $Ar^4$ independently represent an aryl group (the aryl group may have 1 to 5 of the same or different substituents), *1, *2, *3 and *4 indicate asymmetric carbons, and relative steric configurations thereof are in cis-configuration between *1 and *2, cis-configuration between *3 and *4, and trans-configuration between *2 and *3].

According to preferred embodiments of the aforementioned invention, there are provided the aforementioned compound, wherein $Ar^1$, $Ar^2$, $Ar^3$ and $Ar^4$ independently represent phenyl group (said phenyl group may have 1 to 5 of the same or different substituents); and the aforementioned compound, wherein $Ar^1$, $Ar^2$, $Ar^3$ and $Ar^4$ independently represent a 3,5-dialkyl-4-alkoxyphenyl group; and the aforementioned compound, wherein $Ar^1$, $Ar^2$, $Ar^3$ and $Ar^4$ independently represent 3,5-dimethyl-4-methoxyphenyl group.

According to more preferred embodiments, there are provided the aforementioned compound, wherein $R^1$ is hydrogen atom, and $R^2$ is a hydroxyalkyl group, preferably hydroxymethyl group; the aforementioned compound, wherein $R^1$ is hydrogen atom, or an alkyl group, preferably hydrogen atom, or methyl group, and $R^2$ is a triphenylmethyloxyalkyl group, preferably triphenylmethyloxymethyl group; the aforementioned compound, wherein $R^1$ and $R^2$ combine together to represent —C($R^3$)($R^4$)— ($R^3$ and $R^4$ both represent hydrogen atom, or $R^3$ and $R^4$ combine together to represent oxo group); and the aforementioned compound, wherein $R^1$ and $R^2$ combine together to represent —C($R^5$)($R^6$)—O—C($R^7$)($R^8$)— ($R^5$ and $R^6$ independently represent an alkyl group, preferably both represent methyl group, and both $R^7$ and $R^8$ are hydrogen atoms).

From other aspects, there are provided a transition metal complex consisting of a compound represented by the aforementioned general formula (I) and a transition metal, preferably a transition metal selected from the group consisting of rhodium, ruthenium, iridium, and palladium, and an asymmetric catalyst comprising the transition metal complex. This asymmetric catalyst can be used as a catalyst for a catalytic asymmetric hydrogenation reaction of double bonds in olefins, imines, ketones, or the like, and an asymmetric 1,4-addition reaction of enones.

From further aspects, the present invention also provides a phosphine borane compound consisting of a compound represented by the aforementioned general formula (I) having boranes added on each of the two phosphorus atoms of the compound of the general formula (I), and a method for preparing a compound represented by the aforementioned general formula (I), which comprises the step of treating the phosphine borane compound with a base.

EFFECT OF THE INVENTION

The compound represented by the general formula (I) provided by the present invention is useful as an optically active phosphine ligand which can be conveniently synthesized and provides a transition metal complex superior in asymmetric catalyst activity. The transition metal complex comprising this optically active phosphine ligand and a transition metal is useful as a catalyst of a catalytic asymmetric hydrogenation reaction of a double bond. The catalyst is extremely useful especially as an asymmetric reduction catalyst for preparation of N-protected amino acids or alkyl succinates by an asymmetric hydrogenation reaction.

BEST MODE FOR CARRYING OUT THE INVENTION

As the alkyl group, for example, a linear, branched or cyclic alkyl group or alkyl group consisting of a combination thereof having 1 to 20, preferably 1 to 12, more preferably 1 to 6 carbon atoms may be used. More specifically, examples include, for example, methyl group, ethyl group, n-propyl group, isopropyl group, tert-butyl group, cyclohexyl group, and the like, but not limited to these examples. The same shall apply to alkyl moieties in other substituents having the alkyl moiety (hydroxyalkyl group, alkoxyl group, and the like). The alkyl group or the aforementioned alkyl moiety may be substituted.

As the aryl group, a monocyclic or polycyclic aromatic hydrocarbon can be used, and examples include, for example, phenyl group, naphthyl group, and the like. The same shall apply to aryl moieties in other substituents having the aryl moiety (e.g., triarylmethyloxyalkyl group and the like). The aryl group or the aforementioned aryl moiety may be substituted. The aforementioned alkyl group, alkyl moiety, aryl group, and aryl moiety may be substituted. Type, number, and substitution position of the substituent are not particularly limited, and examples of the substituent include, for example, hydroxyl group, an alkyl group, an alkoxyl group, amino group, an alkylamino group, nitro group, cyano group, an aryl group, a halogen atom and the like.

$R^1$ represents hydrogen atom, or an alkyl group. As $R^1$, hydrogen atom, or an alkyl group having 1 to 6 carbon atoms is preferred, hydrogen atom, or an alkyl group having 1 to 3 carbon atoms is more preferred, and hydrogen atom or methyl group is still more preferred.

$R^2$ represents a hydroxyalkyl group, or a triarylmethyloxyalkyl group. Although number of the hydroxyl group existing in the hydroxyalkyl group represented by $R^2$ is not particularly limited, it is preferably, for example, 1 or 2, particularly preferably 1. As the hydroxyalkyl group represented by $R^2$, a monohydroxyalkyl group having 1 to 6 carbon atoms is preferred, a monohydroxyalkyl group having 1 to 3 carbon atoms is more preferred, and hydroxymethyl group is particularly preferred. As the triarylmethyloxyalkyl group represented by $R^2$, an alkyl group having 1 to 6 carbon atoms substituted with triphenylmethyloxy group is preferred, an alkyl group having 1 to 3 carbon atoms substituted with triphenylmethyloxy group is more preferred, and triphenylmethyloxymethyl group is particularly preferred.

$R^1$ and $R^2$ may combine together to form a group represented by —C($R^3$)($R^4$)— or —C($R^5$)($R^6$)—O—C($R^7$)($R^8$)— (the left end of the group represented by —C($R^5$)($R^6$)—O—C($R^7$)($R^8$)— directly bonds to the oxygen atom to which $R^1$ binds). In this case, a 5-member ring and 7-member ring each containing one ring-constituting oxygen atom are formed. $R^3$ and $R^4$ independently represent hydrogen atom, an alkyl group, or hydroxyl group, or $R^3$ and $R^4$ may combine together to represent oxo group. As the alkyl group represented by $R^3$ or $R^4$, an alkyl group having 1 to 6 carbon atoms is preferred, an alkyl group having 1 to 3 carbon atoms is more preferred, and methyl group is still more preferred. It is preferred that both $R^3$ and $R^4$ are hydrogen atoms. It is also preferred that $R^3$ and $R^4$ combine together to represent oxo group.

$R^5, R^6, R^7$, and $R^8$ independently represent hydrogen atom, an alkyl group, or hydroxyl group. $R^5$ and $R^6$ may combine together to represent oxo group, and/or $R^7$ and $R^8$ may combine together to represent oxo group. As the alkyl group represented by $R^5, R^6, R^7$, or $R^8$, an alkyl group having 1 to 6 carbon atoms is preferred, an alkyl group having 1 to 3 carbon atoms is more preferred, and methyl group is still more preferred. It is preferred that $R^5$ and $R^6$ are the same or different alkyl groups having 1 to 6 carbon atoms, it is more preferred that $R^5$ and $R^6$ are the same or different alkyl groups having 1 to 3 carbon atoms, and it is still more preferred that $R^5$ and $R^6$ are methyl groups. When $R^5$ and $R^6$ are the same or different alkyl groups, it is preferred that $R^7$ and $R^8$ are hydrogen atoms. It is particularly preferred that $R^5$ and $R^6$ are the same or different alkyl groups having 1 to 6 carbon atoms, preferably alkyl groups having 1 to 3 carbon atoms, still more preferably methyl groups, and $R^7$ and $R^8$ are hydrogen atoms.

In the aforementioned general formula (I), it is particularly preferred that $R^1$ is hydrogen atom, and $R^2$ is a hydroxyalkyl group, preferably hydroxymethyl group; $R^1$ is hydrogen atom, or an alkyl group, preferably hydrogen atom, or methyl group, and $R^2$ is a triphenylmethyloxyalkyl group, preferably triphenylmethyloxymethyl group; $R^1$ and $R^2$ combine together to represent —C($R^3$)($R^4$)— ($R^3$ and $R^4$ are hydrogen atoms, or $R^3$ and $R^4$ combine together to represent oxo group); or $R^1$ and $R^2$ combine together to represent —C($R^5$)($R^6$)—O—C($R^7$)($R^8$)— ($R^5$ and $R^6$ independently represent an alkyl group, preferably both represent methyl group, and $R^7$ and $R^8$ are hydrogen atoms).

$Ar^1, Ar^2, Ar^3$, and $Ar^4$ independently represent an aryl group, preferably a phenyl group. The aryl group represented by $Ar^1, Ar^2, Ar^3$, or $Ar^4$ may have 1 to 5 of the same or different substituents. As the substituent, an alkyl group and an alkoxyl group are preferred, but not limited to these examples. It is preferred that, for example, the aryl group represented by $Ar^1, Ar^2, Ar^3$, or $Ar^4$, preferably phenyl group, has 1 to 3 of alkyl groups having 1 to 6 carbon atoms, preferably alkyl groups having 1 to 3 carbon atoms, more preferably methyl groups, and 1 alkoxyl group having 1 to 6 carbon atoms, preferably alkoxyl group having 1 to 3 carbon atoms, more preferably methoxy group. As the aryl group represented by $Ar^1, Ar^2, Ar^3$, or $Ar^4$, for example, phenyl group, 3,5-dimethyl-4-methoxyphenyl group and the like are particularly preferred.

In the compound represented by the aforementioned general formula (I), *1, *2, *3 and *4 indicate asymmetric carbons, and relative steric configurations of the asymmetric carbons are in cis-configuration between *1 and *2, cis-configuration between *3 and *4, and trans-configuration between *2 and *3. The compound represented by the aforementioned general formula (I) is preferably provided as an optically active compound.

Examples of the compound represented by the aforementioned general formula (I) are mentioned below. However, the compound of the present invention is not limited to these examples. In the formulas, Ph represents phenyl group, Me represents methyl group, and Ar represents 3,5-dimethyl-4-methoxyphenyl group.

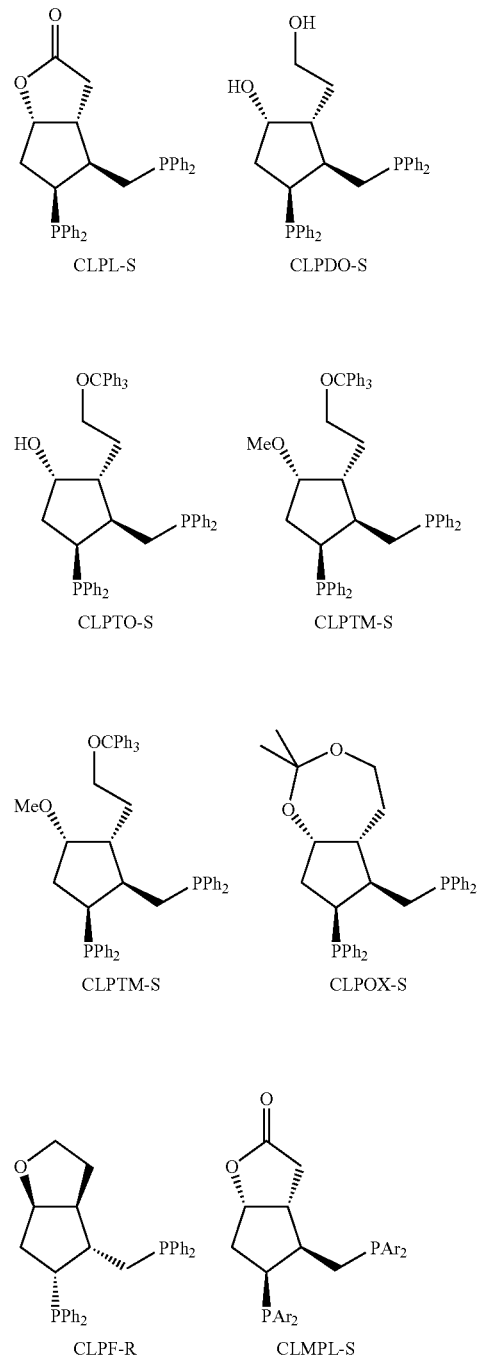

According to the present invention, a phosphine borane compound consisting of a compound represented by the aforementioned general formula (I) having boranes added on each of the two phosphorus atoms of the compound is provided. This borane compound is useful as an intermediate for the preparation of the compound represented by the general formula (I). More specifically, the following compounds are provided as the borane compounds corresponding to the preferred examples of the compound represented by the general formula (I) mentioned above. However, the borane compound is not limited to the following specific compounds.

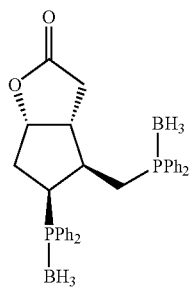

(3)

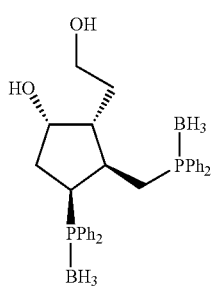

(4)

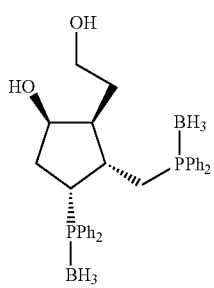

(enantiomer of 4)

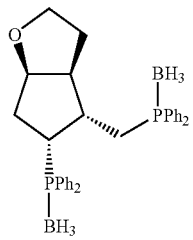

(5)

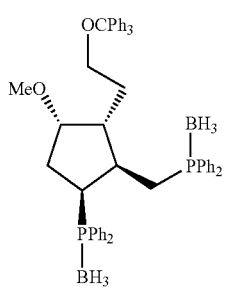

(7)

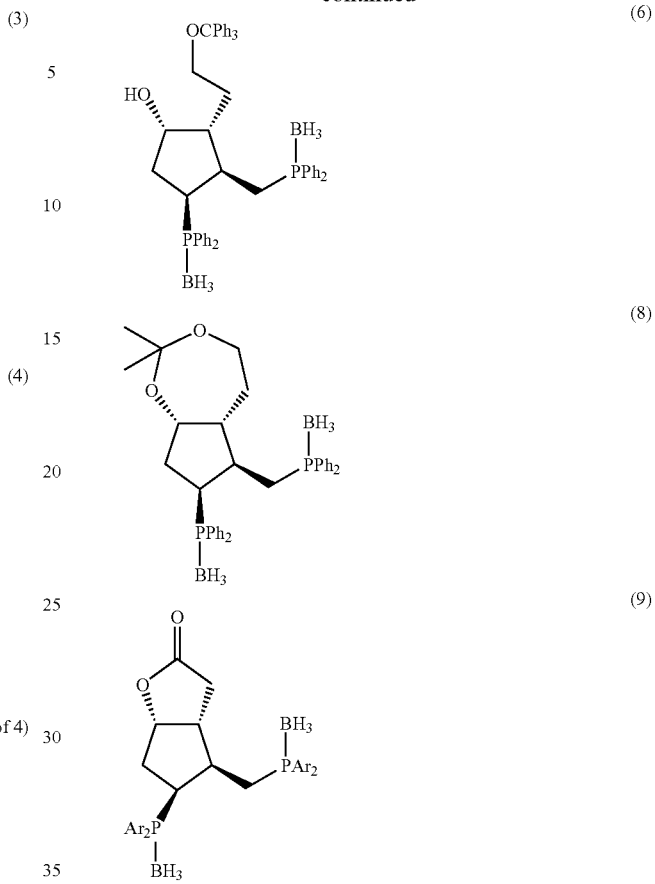

Although the method for preparing the compound represented by the aforementioned general formula (I) is not particularly limited, the compounds mentioned above as preferred compounds can be prepared by, for example, the methods shown below. The details of these methods are explained in the examples, and accordingly, those skilled in the art can easily understand that arbitrary compounds falling within the scope of the compound represented by the general formula (I) can be prepared by referring to the following general explanations and examples. In the following schemes, Ts represents para-toluenesulfonyl group, Ph represents phenyl group, Me represents methyl group, Et represents ethyl group, n-Bu represents n-butyl group, DABCO represents 1,4-diazobicyclo[2,2,2]octane, THF represents tetrahydrofuran, DMF represents dimethylformamide, and regents and solvents mentioned in the reaction steps are typical examples.

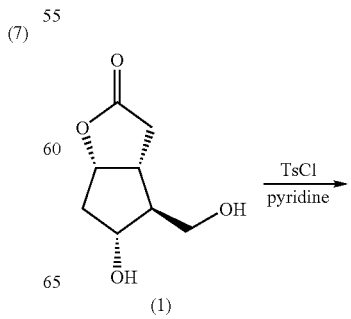

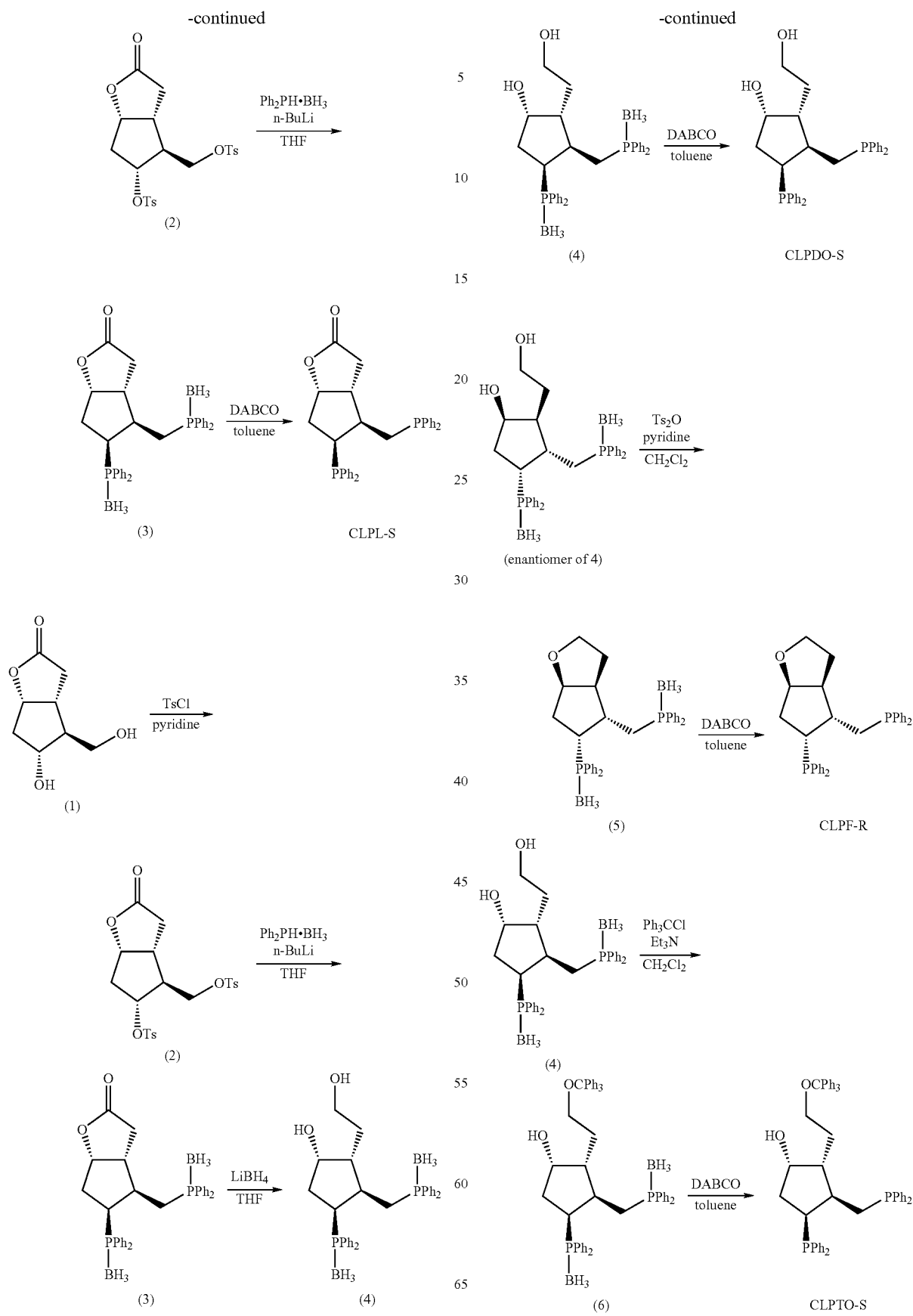

-continued

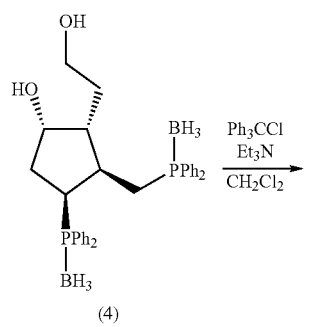
(4)

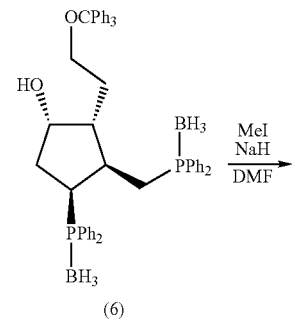
(6)

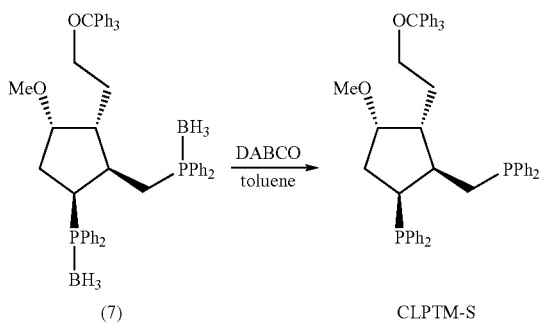
(7)    CLPTM-S

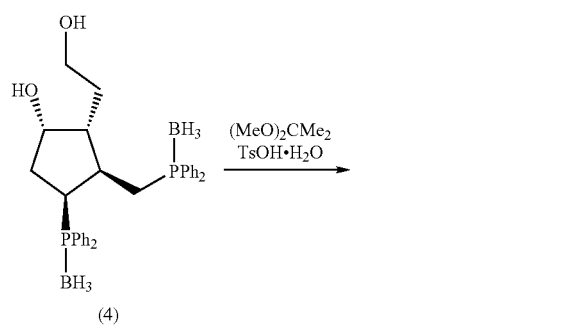
(4)

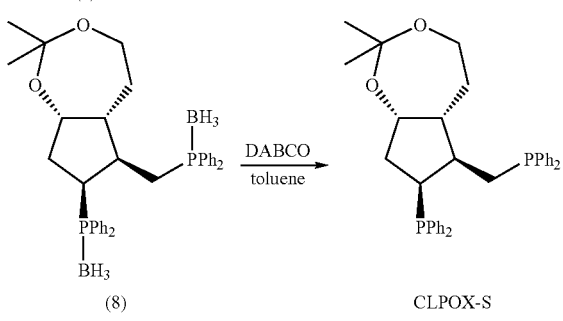
(8)    CLPOX-S

-continued

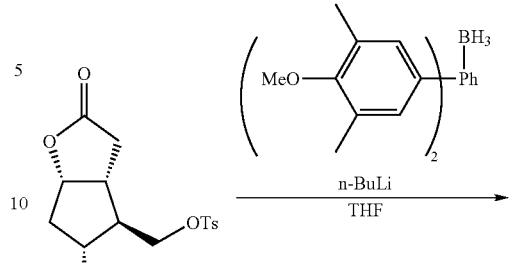
(2)

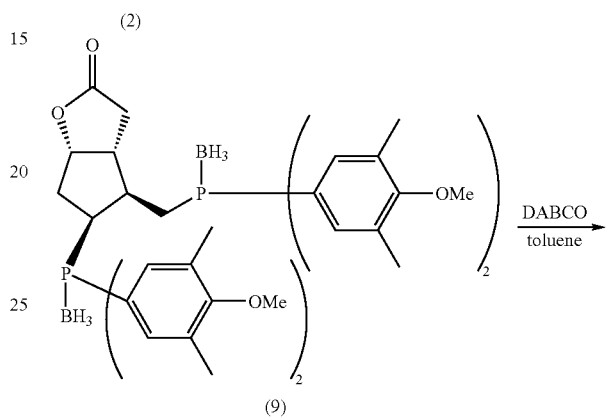
(9)

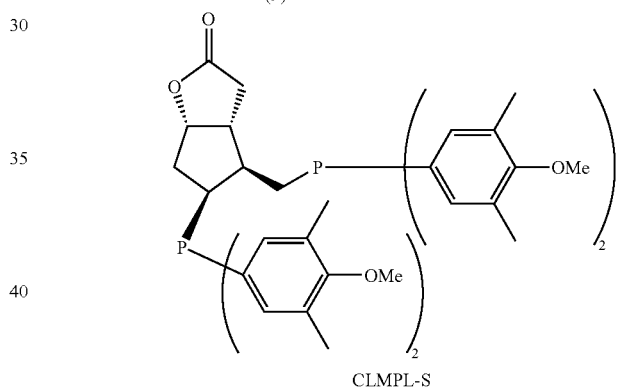
CLMPL-S

Compound (1) mentioned above as a starting material is called as "Corey lactone" and widely used as an intermediate in the synthesis of naturally-occurring type prostaglandins, and can be prepared by, for example, the method described in J. Am. Chem. Soc., 91(20), pp. 5675-5677, 1969.

For the sulfonic acid esterification (for example, conversion of Compound (1) into Compound (2) mentioned above), sulfonic acid halides, sulfonic acid anhydrides, and the like can be used. Examples include, for example, methanesulfonyl chloride, ethanesulfonyl chloride, trichloromethanesulfonyl chloride, benzenesulfonyl chloride, 2-nitrobenzenesulfonyl chloride, camphorsulfonyl chloride, trifluoromethanesulfonic anhydride, methanesulfonic anhydride, p-toluenesulfonic anhydride, and the like. The sulfonic acid esterification can be performed by a treatment with a sulfonic acid esterification agent in the presence of a basic compound. As the basic compound are, for example, inorganic basic compounds such as sodium carbonate and potassium carbonate, triethylamine, diisopropylethylamine, pyridine, 1,8-diazabicyclo[5.4.0]-7-undecene, 1,4-diazabicyclo[2.2.2]octane, and the like may be used.

Examples of the solvent used for the sulfonic acid esterification include, for example, saturated hydrocarbons such as hexane, heptane, cyclohexane and methylcyclohexane, aromatic solvents such as benzene, toluene, anisole and chlorobenzene, ethers such as tetrahydrofuran, diethyl ether and cyclopentyl methyl ether, halogen type solvents such as chloroform, dichloromethane and carbon tetrachloride, and amides such as N,N-dimethylformamide, N,N-diethylacetamide and hexamethylphosphoric triamide, as well as solvents consisting a mixture of these at an arbitrary ratio, if needed, but the solvents are not limited to these examples. The volume of the solvent is 0.1 to 1000 times, preferably 1 to 100 times, based on the volume of the substrate compound. The reaction temperature is usually −20 to 100° C. Although the reaction time may vary depending on the solvent, temperature, concentration and the like, it is determined on the basis of the time required to consume the reaction substrate, and is usually from 30 minutes to 24 hours.

The phosphination (for example, conversion of Compound (2) into Compound (3) mentioned above) can be performed by, for example, reacting an anion of diphenylphosphine borane. The anion of diphenylphosphine borane can be obtained by reacting diphenylphosphine borane with an arbitrary anionizing agent such as alkali metals and alkali metal compounds. Examples of the anionizing agent include, for example, simple substances of alkali metals such as metal sodium and metal potassium, solutions of methyllithium, phenyllithium, n-butyllithium, sec-butyllithium, and tert-butyllithium, dispersion of sodium hydride, potassium tert-butoxide, and the like. Examples of the solvent include, for example, saturated hydrocarbons such as heptane, hexane, cyclohexane and methylcyclohexane, aromatic solvents such as benzene, toluene and anisole, ethers such as tetrahydrofuran, diethyl ether and cyclopentyl methyl ether, halogen type solvents such as chloroform, dichloromethane and carbon tetrachloride, amides such as N,N-dimethylformamide, N,N-diethylacetamide and hexamethylphosphoric triamide, or if needed, a solvent as a mixture thereof at an arbitrary ratio, however the solvents are not limited to these examples. The volume of the solvent is 0.1 to 1000 times, preferably 1 to 100 times, based on the volume of the substrate. The reaction temperature is usually −100 to 100° C. Although the reaction time may vary depending on the solvent, temperature, concentration and the like, the time is determined on the basis of the time required to consume the reaction substrate, and is usually from 1 to 24 hours.

The deboranation reaction (for example, conversion of Compound (3) into CLPL-S mentioned above) can be performed by allowing a base compound such as amine to react on the borane compound obtained by the phosphination. As the base compound, for example, various organic amines can be used, and more specifically, examples include, for example, diethylamine, morpholine, pyrrolidine, piperidine, triethylamine, 1,8-diazabicyclo[5.4.0]-7-undecene, 1,4-diazabicyclo[2.2.2]octane, and the like. Although the deboranation reaction may be performed without solvent, a solvent may be used. Examples of the solvent include, for example, saturated hydrocarbons such as heptane, hexane, cyclohexane and methylcyclohexane, aromatic solvents such as benzene, toluene, anisole and chlorobenzene, ethers such as tetrahydrofuran, diethyl ether and cyclopentyl methyl ether, and amides such as N,N-dimethylformamide, N,N-diethylacetamide and hexamethylphosphoric triamide, or if needed, a solvent as a mixture thereof at an arbitrary ratio. The volume of the solvent is 0.1 to 1000 times, preferably 1 to 100 times, based on the volume of the substrate. The reaction temperature is usually −20 to 150° C. Although the reaction time may vary depending on the solvent, temperature, concentration and the like, the time is determined on the basis of the time required to consume the reaction substrate, and is usually from 10 minutes to 24 hours.

The ring opening of the lactone ring (for example, conversion of Compound (3) into Compound (4) mentioned above) can be performed by reduction using a hydride compound. Examples of the hydride compound include, for example, lithium aluminum hydride, lithium borohydride, sodium borohydride, sodium bismethoxyethoxydihydroaluminate toluene solution, and the like. Although the solvent used in the reduction reaction is not particularly limited, examples of the solvent include, for example, saturated hydrocarbons such as heptane, hexane, cyclohexane and methylcyclohexane, aromatic solvents such as benzene, toluene, anisole and chlorobenzene, and ethers such as tetrahydrofuran, diethyl ether and cyclopentyl methyl ether, or if needed, a solvent as a mixture thereof at an arbitrary ratio. The volume of the solvent is 0.1 to 1000 times, preferably 1 to 100 times, based on the volume of the substrate. The reaction temperature is usually −100 to 100° C. Although the reaction time may vary depending on the solvent, temperature, concentration and the like, the time is determined on the basis of the time required to consume the reaction substrate, and is usually from 1 to 24 hours.

The etherification (for example, conversion of Compound (6) into Compound (7) mentioned above) can be performed by various generally known etherification methods. Examples include, for example, methods utilizing an alkylating agent such as alkyl halides, sulfuric acid alkyl esters and sulfonic acid alkyl esters, an aralkylating agent such as aralkyl halides, sulfuric acid aralkyl esters and sulfonic acid aralkyl esters, or an arylating agent such as aryl halides, and a basic compound, but the methods are not limited to these examples. Examples of the alkylating agent such as alkyl halides, sulfuric acid alkyl esters and sulfonic acid alkyl esters include, for example, iodomethane, ethyl bromide, isopropyl bromide, dimethyl sulfate, diethyl sulfate, methyl p-toluenesulfonate, methyl trifluoromethanesulfonate, and the like. Examples of the aralkyl halides, sulfuric acid aralkyl esters and sulfonic acid aralkyl esters include, for example, benzyl bromide, triphenylmethane chloride, dibenzyl sulfate, benzyl methanesulfonate, and the like. Examples of the arylating agent such as aryl halides include, for example, iodobenzene, bromotoluene, iodonaphthalene, and the like. As the basic compound, for example, alkali metal compounds, organic bases, and the like can be used. Examples include, for example, sodium hydroxide, potassium hydroxide, sodium carbonate, potassium carbonate, cesium carbonate, sodium hydride, potassium tert-butoxide, triethylamine, 1,8-diazabicyclo[5.4.0]-7-undecene, 1,4-diazabicyclo[2.2.2]octane, and the like, but the basic compounds are not limited to these examples. In the case of the arylation, a transition metal compound such as copper(1) iodide and copper(1) bromide can also be used as the catalyst as well as the aforementioned basic compounds.

Examples of the solvent used for the etherification include, for example, saturated hydrocarbons such as heptane, hexane, cyclohexane and methylcyclohexane, aromatic solvents such as benzene, toluene, anisole and chlorobenzene, ethers such as tetrahydrofuran, diethyl ether and cyclopentyl methyl ether, halogen type solvents such as chloroform, dichloromethane and carbon tetrachloride, and amides such as N,N-dimethylformamide, N,N-diethylacetamide and hexamethylphosphoric triamide, or if needed, a solvent as a mixture thereof at an arbitrary ratio. The volume of the solvent is 0.1 to 1000 times, preferably 1 to 100 times, based on the volume of the substrate compound. The reaction temperature is usually −20 to 150° C. Although the reaction time may vary depending on the solvent, temperature, concentration and the like, the time is determined on the basis of the time required to consume the reaction substrate, and is usually from 30 minutes to 24 hours.

The oxepane cyclization reaction (for example, conversion of Compound (4) into Compound (8) mentioned above) can be performed by reacting a diol compound with a ketone, an aldehyde, or a derivative thereof under an acidic condition. Examples of the ketone or ketone derivative include, for example, acetone, 2-butanone, 3-pentanone, cyclohexanone, 2,2-dimethoxypropane, 2,2-diethoxypropane, 2,2-dimethyl-1,3-oxolane, and the like. Examples of the aldehyde or aldehyde derivative include, for example, formaldehyde, isopropylaldehyde, benzaldehyde, 1,1-dimethoxyethane, 1,1-dimethoxy-2-methylethane, and the like. The acid is not particularly limited, and examples include hydrochloric acid, sulfuric acid, p-toluenesulfonic acid, methanesulfonic acid, strongly acidic ion exchange resins, and the like. Although reactants may serve as a solvent, the reaction may be performed by using a solvent. For example, solvents such as saturated hydrocarbons such as heptane, hexane, cyclohexane and methylcyclohexane, aromatic solvents such as benzene, toluene, anisole and chlorobenzene, ethers such as tetrahydrofuran, diethyl ether and cyclopentyl methyl ether, halogen type solvents such as chloroform, dichloromethane and carbon tetrachloride, and amides such as N,N-dimethylformamide, N,N-diethylacetamide and hexamethylphosphoric triamide, or if needed, a solvent as a mixture thereof at an arbitrary ratio may be used. The volume of the solvent is 0.1 to 1000 times, preferably 1 to 100 times, based on the volume of the substrate. The reaction temperature is usually −20 to 150° C.

The cyclization reaction of the diol compound using a sulfonic acid compound (for example, conversion of Compound (4) into Compound (5) mentioned above) can be performed in the presence of a basic compound. As the sulfonic acid compound, sulfonic acid halides, sulfonic acid anhydrides, and the like can be used. Examples include, for example, methanesulfonyl chloride, ethanesulfonyl chloride, trichloromethanesulfonyl chloride, p-toluenesulfonyl chloride, benzenesulfonyl chloride, 2-nitrobenzenesulfonyl chloride, camphorsulfonyl chloride, trifluoromethanesulfonic anhydride, methanesulfonic anhydride, p-toluenesulfonic anhydride, and the like. Examples of the basic compound include, for example, inorganic basic compounds such as sodium carbonate and potassium carbonate, triethylamine, diisopropylethylamine, pyridine, 1,8-diazabicyclo[5.4.0]-7-undecene, 1,4-diazabicyclo[2.2.2]octane, and the like. Examples of the solvent include, for example, saturated hydrocarbons such as hexane, heptane, cyclohexane and methylcyclohexane, aromatic solvents such as benzene, toluene, anisole and chlorobenzene, ethers such as tetrahydrofuran, diethyl ether and cyclopentyl methyl ether, halogen type solvents such as chloroform, dichloromethane and carbon tetrachloride, and amides such as N,N-dimethylformamide, N,N-diethylacetamide and hexamethylphosphoric triamide, or if needed, a solvent as a mixture thereof at an arbitrary ratio. The volume of the solvent is 0.1 to 1000 times, preferably 1 to 100 times, based on the volume of the substrate. The reaction temperature is usually −20 to 100° C. Although the reaction time may vary depending on the solvent, temperature, concentration and the like, the time is determined on the basis of the time required to consume the reaction substrate, and is usually from 30 minutes to 24 hours.

The compound represented by the aforementioned general formula (I) provided by the present invention is useful as a ligand of a transition metal complex. As the transition metal contained in the transition metal complex provided by the present invention, the transition metals of the 4th and 5th periods, preferably rhodium (Rh), ruthenium (Ru), iridium (Ir), and palladium (Pd), can be used. The aforementioned transition metal complex can be obtained by reacting or mixing a transition metal with the compound represented by the aforementioned general formula (I). The aforementioned complex is a complex compound of a transition metal atom and the molecule of the compound represented by the aforementioned general formula (I) in a ratio of 1:1 to 1:5, preferably 1:1. This transition metal complex can be used as a catalyst for a catalytic asymmetric hydrogenation reaction as explained below, and for use as a catalyst, the complex may be an isolated complex, or in the form of a solution or slurry after preparation of the transition metal complex in a reaction system.

When rhodium is used as the transition metal, for the preparation and isolation of the complex, the method described in "Organic Metal Complex", Jikken Kagaku Koza (Lecture of Experimental Chemistry), 4th edition, edited by the Chemical Society of Japan, vol. 18, pp. 339-344, 1991, Maruzen can be referred to. For the preparation of the rhodium complex, for example, the following rhodium compounds can be used (in the formulas, L represents the compound represented by the general formula (I), cod represents 1,5-cyclooctadiene, and nbd represents norbornadiene): [Rh(cod)(L)]BF$_4$, [Rh(cod)(L)]ClO$_4$, [Rh(cod)(L)]PF$_6$, [Rh(cod)(L)]OSO$_2$CF$_3$, [Rh(nbd)(L)]BF$_4$, [Rh(nbd)(L)]ClO$_4$, [Rh(nbd)(L)]PF$_6$, [Rh(nbd)(L)]OSO$_2$CF$_3$. Further, when the rhodium complex is used without isolation, a rhodium compound and the compound represented by the general formula (I) can be dissolved and reacted in an appropriate solvent, and the reaction mixture without any treatment or the reaction mixture concentrated by an appropriate means can be used. Examples of the rhodium compound usable in such a case include, for example, the following compounds (in the formulas, cod and nbd have the same meanings as those mentioned above, and acac represents acetylacetonato): [Rh(cod)$_2$] BF$_4$, [Rh(cod)$_2$]ClO$_4$, [Rh(cod)$_2$]PF$_6$, [Rh(cod)$_2$]OSO$_2$CF$_3$, [Rh(nbd)$_2$]BF$_4$, [Rh(nbd)$_2$]ClO$_4$, [Rh(nbd)$_2$]PF$_6$, [Rh(nbd)$_2$]OSO$_2$CF$_3$, [RhCl(cod)]$_2$, [RhCl(nbd)]$_2$, [Rh(acac)(cod)].

Examples of the solvent include, for example, alcohols such as methanol, ethanol, 2-propanol, 2-methyl-2-propanol and cyclohexanol, saturated hydrocarbons such as heptane, hexane, cyclohexane and methylcyclohexane, aromatic solvents such as benzene, toluene, anisole and chlorobenzene, ethers such as tetrahydrofuran, diethyl ether and cyclopentyl methyl ether, halogen type solvents such as chloroform, dichloromethane and carbon tetrachloride, and amides such as N,N-dimethylformamide, N,N-diethylacetamide and hexamethylphosphoric triamide, or if needed, a solvent as a mixture thereof at an arbitrary ratio, however, the solvents are not limited to these examples.

When ruthenium is used as the transition metal, for the preparation and isolation of the complex, the method described in M. Kitamura, Org. Synth., 71, pp. 1-13 can be referred to, and as described in the publication, a method of heating the compound represented by the general formula (I) with [Ru(cod)Cl$_2$]$_n$ in dimethylformamide (DMF), or the like can be employed.

When palladium is used as the transition metal, for the preparation and isolation of the complex, the method described in Sato F., "Gosei Kagakusha no tameno Jikken Yuki Kinzoku Kagaku (Experimental Organic Metal Chemistry for Synthetic Chemists)", pp. 195-196, Kodansha, 1992 can be referred to, and as described in the publication, the complex can be prepared by mixing the compound represented by the general formula (I) with [PdCl$_2$(MeCN)$_2$] in benzene.

When iridium is used as the transition metal, for the preparation and isolation of the complex, the method described in "Organic Metal Complex", Jikken Kagaku Koza (Lecture of Experimental Chemistry), 4th edition, edited by the Chemical Society of Japan, vol. 18, p. 363, 1991, Maruzen can be referred to. For the preparation of the iridium complex, for example, the following rhodium compounds can be used (L, cod and nbd have the same meanings as those mentioned above): [Ir(cod)(L)]BF$_4$, [Ir(cod)(L)]ClO$_4$, [Ir(cod)(L)]PF$_6$, [Ir(cod)(L)]OSO$_2$CF$_3$, [Ir(nbd)(L)]BF$_4$, [Ir(nbd)(L)]ClO$_4$, [Ir(nbd)(L)]PF$_6$, [Ir(nbd)(L)]OSO$_2$CF$_3$. Further, when the iridium complex is used without isolation, an iridium compound and the compound represented by the general formula (I) can be dissolved and reacted in an appropriate solvent, and the reaction mixture can be used without any treatment or the reaction mixture concentrated by an appropriate means can be used. Examples of the iridium compound used in the above case include, for example, the following compounds (in the formulas, cod, nbd and acac have the same meanings as those mentioned above): [Ir(cod)$_2$]BF$_4$, [Ir(cod)(L)]ClO$_4$, [Ir(cod)$_2$] PF$_6$, [Ir(cod)$_2$]OSO$_2$CF$_3$, [Ir(nbd)$_2$]BF$_4$, [Ir(nbd)$_2$] ClO$_4$, [Ir(nbd)$_2$]PF$_6$, [Ir(nbd)$_2$]OSO$_2$CF$_3$, [IrCl(cod)]$_2$, [IrCl(nbd)]$_2$, [Ir(acac)(cod)]. As the solvent, the same solvents as those mentioned above for the case of rhodium can be used.

The aforementioned transition metal complex consisting of a transition metal atom and the compound represented by the aforementioned general formula (I) as a ligand is useful as, for example, a catalyst of a catalytic asymmetric hydrogenation reaction. Examples of a chemical bond which can be reduced by the catalytic asymmetric hydrogenation reaction include, for example, carbon-carbon double bond, carbon-carbon triple bond, carbon-nitrogen double bond, carbon-oxygen double bond, and the like. Among them, preferred reactions include reductions of an olefin (C=C), an imine (C=N), and a ketone (C=O). By performing a catalytic asymmetric hydrogenation reaction using the asymmetric catalyst containing the transition metal complex of the present invention, an unsaturated bond can be stereoselectively reduced, and thus an optical isomer with a high optical purity can be easily prepared. For example, by carrying out asymmetric hydrogenation of an alkylidene succinate derivative using the catalyst of the present invention, an alkyl succinate derivative with a high optical purity can be easily prepared. Further, by carrying out asymmetric hydrogenation of an N-protected aminoacrylate derivative using the catalyst of the present invention, a protected amino acid derivative with a high optical purity can be easily prepared.

A molar ratio of a substrate containing an unsaturated bond and the complex as a catalyst (S/C) is, for example, about 100 to 100,000. The catalytic asymmetric hydrogenation can be performed at a reaction temperature of, for example, about −20 to 200° C., preferably 0 to 80° C. Hydrogen pressure may be, for example, about 0.01 to 25 MPa, preferably 0.1 to 10 MPa. The reaction solvent can be suitably chosen from viewpoints of stability, reactivity and the like of the substrate. For example, alcohols such as methanol, ethanol, 2-propanol, 2-methyl-2-propanol and cyclohexanol, saturated hydrocarbons such as heptane, hexane, cyclohexane and methylcyclohexane, aromatic solvents such as benzene, toluene, anisole and chlorobenzene, ethers such as tetrahydrofuran, diethyl ether and cyclopentyl methyl ether, halogen type solvents such as chloroform, dichloromethane and carbon tetrachloride, and amides such as N,N-dimethylformamide, N,N-diethylacetamide and hexamethylphosphoric triamide, or if needed, a solvent as a mixture thereof at an arbitrary ratio may be used.

Examples of the asymmetric reaction using the catalyst of the present invention are shown below. However, the reactions are not limited to these examples (in the formula, Me represents methyl group, Ph represents phenyl group, Ac represents acetyl group, R represents a protective group of carboxylic acid such as an alkyl group, and * indicates an asymmetric carbon)

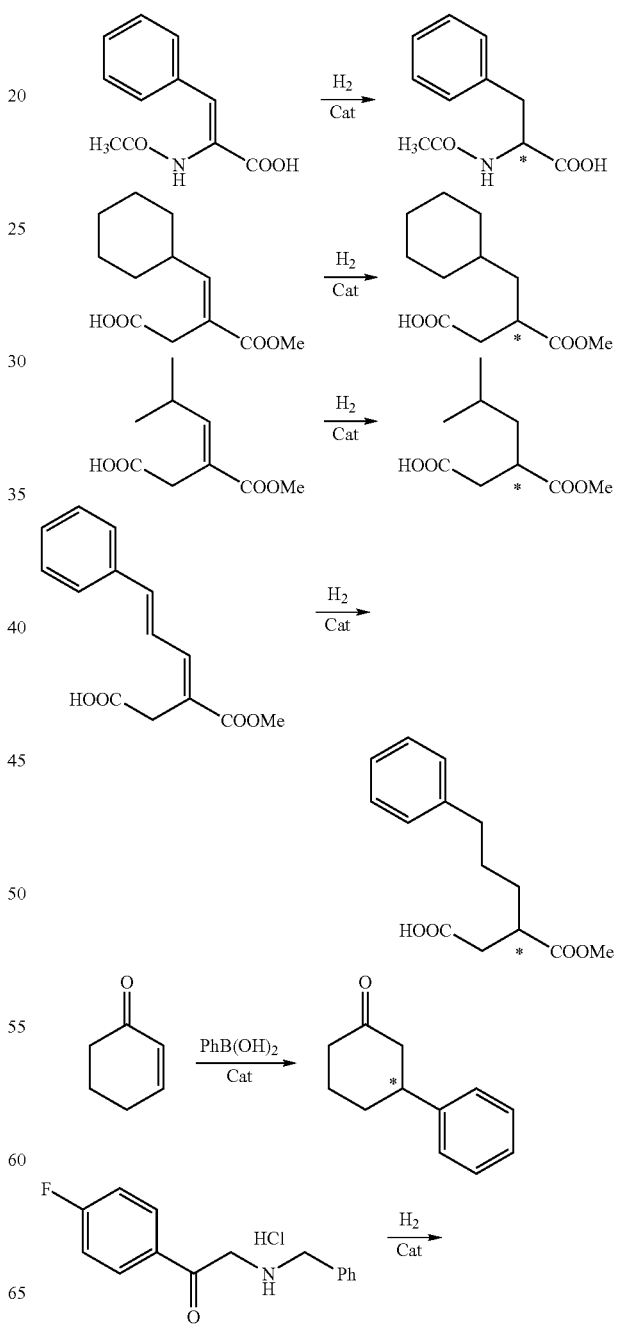

-continued

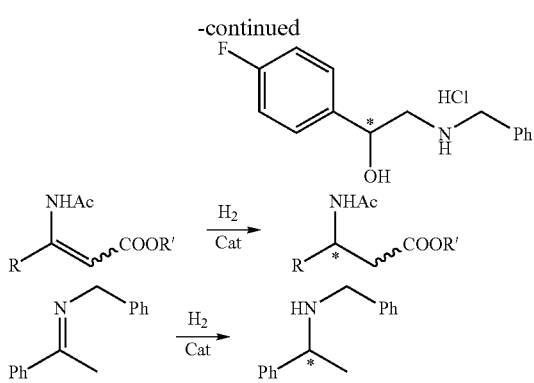

EXAMPLES

The present invention will be more specifically explained with reference to examples. However, the scope of the present invention is not limited by the following examples. In the following examples, the abbreviations of the compounds (CLPL-S and the like) and the numbers of the compounds are the same as those used for the preferred compounds mentioned above.

Example 1

Preparation of (3aR,4S,5R,6aS)-5-p-toluenesulfoxy-4-[(p-toluenesulfoxy)methyl]hexahydrocyclopenta[b]furan-2-one (Compound 2)

To a 200 mL-three-neck flask attached with a dropping funnel were added p-toluenesulfonyl chloride (37.0 g, 190 mmol), and 60 mL of pyridine, and the mixture was cooled on an ice bath. The mixture was added dropwise with a solution of (3aR,4S,5R,6aS)-5-hydroxy-4-hydroxymethylhexahydrocyclopenta[b]furan-2-one (Compound 1, 8.6 g, 50 mmol) in 40 mL of pyridine, stirred for 30 minutes, then warmed to room temperature, and further stirred for 2.5 hours. The mixture was again cooled on an ice bath, and slowly added with 50 mL of ice water. The mixture was stirred at room temperature for 10 minutes, and then added with 80 mL of ethyl acetate, the layers were separated, and further the aqueous layer was extracted twice with 30 mL of ethyl acetate. The organic layers were combined, and washed five times with 50 mL of diluted hydrochloric acid and once with 40 mL of saturated brine in this order. The organic layer was dried over anhydrous magnesium sulfate, and after the drying agent was removed by filtration, concentrated in an evaporator. The residue was added with 150 mL of methanol, and the mixture was stirred at 70° C. for 30 minutes with heating, and then crystallized at 5 to 10° C. by cooling. The precipitated solid was collected by filtration, and dried in a desiccator to obtain (3aR,4S,5R,6aS)-5-p-toluenesulfoxy-4-[(p-toluenesulfoxy)methyl]hexahydrocyclopenta-[b]furan-2-one (Compound 2) as white crystals (17.5 g, yield: 73%).

$^1$H NMR (CDCl$_3$, 300 MHz): δ 7.77-7.72 (m, 4H), 7.40-7.33 (m, 4H), 4.87-4.76 (m, 2H), 4.04-3.94 (m, 2H), 2.81-2.73 (m, 2H), 2.48 (s, 3H), 2.46 (s, 3H), 2.44-2.26 (m, 3H), 2.26-2.04 (m, 1H)

m.p.: 41 to 43° C.

$[α]_D^{20}$=−57.70 (c=1.02, toluene)

Example 2

Preparation of (3aR,4S,5S,6aS)-(5-diphenylphosphanyl-4-[(diphenylphosphanyl)methyl]hexahydrocyclopenta[b]furan-2-one-borane complex (Compound 3)

To a 200 mL-three-neck flask attached with a dropping funnel and a three-way cock were added diphenylphosphine-borane complex (7.9 g, 39.5 mmol) and 45 mL of dehydrated THF, and the mixture was cooled to −15° C., and slowly added dropwise with a 1.56 mol/L solution of n-butyllithium (25.3 mL, 39.5 mmol) in hexane. The mixture was stirred for 10 minutes, then added dropwise with a solution of (3aR,4S,5R,6aS)-5-p-toluenesulfoxy-4-[(p-toluenesulfoxy)methyl]hexahydrocyclopenta[b]furan-2-one (Compound 2, 7.3 g, 15.2 mmol) in 20 mL of tetrahydrofuran, and stirred at room temperature for 16 hours. The reaction mixture was added with 40 mL of diethyl ether and 20 mL of saturated brine, the layers were separated, and the aqueous layer was extracted twice with 20 mL of diethyl ether. The organic layers were combined, and washed twice with 10 mL of saturated brine. The organic layer was dried over anhydrous magnesium sulfate, and after the drying agent was removed by filtration, concentrated in an evaporator. The residue was purified by silica gel column chromatography (toluene:ethyl acetate=10:1) to obtain (3aR,4S,5S,6aS)-(5-diphenylphosphanyl-4-[(diphenylphosphanyl)methyl]hexahydrocyclopenta[b]furan-2-one-borane complex (Compound 3, 4.41 g, yield: 54%).

$^1$H NMR (CDCl$_3$, 300 MHz): δ 7.79-7.13 (m, 20H), 5.04-5.00 (t, J=5.1 Hz, 1H), 3.28-3.11 (m, 2H), 2.90-2.77 (m, 2H), 2.56-2.38 (m, 1H), 2.35-2.02 (m, 4H), 1.08 (brs, 6H)

$[α]_D^{20}$=−40.94 (c=1.00, toluene)

Example 3

Preparation of (3aR,4S,5S,6aS)-4-diphenylphosphanyl-3-[(diphenylphosphanyl)methyl]-2-(2-hydroxyethyl)cyclopentanol-borane complex (Compound 4)

To a 50 mL-three-neck flask attached with a thermometer and a three-way cock were added lithium borohydride (0.20 g, 9.3 mmol) and 10 mL of dehydrated tetrahydrofuran, and the mixture was cooled on an ice bath. The mixture was added dropwise with a solution of (3aR,4S,5S,6aS)-5-diphenylphosphanyl-4-[(diphenylphosphanyl)methyl]hexahydrocyclopenta[b]furan-2-one-borane complex (Compound 3, 2.5 g, 4.7 mmol) in 15 mL of dehydrated tetrahydrofuran, and stirred at room temperature for 16 hours. The reaction mixture was cooled, added with 15 mL of toluene and 10 mL of diluted hydrochloric acid, and the mixture was stirred for 15 minutes. The layers were separated, the aqueous layer was extracted three times with 5 mL of toluene, and the organic layers were combined, and washed three times with 5 mL of saturated brine. The organic layer was dried over anhydrous magnesium sulfate, and after the drying agent was removed by filtration, concentrated in an evaporator. The residue was purified by silica gel column chromatography (toluene:ethyl acetate=1:1) to obtain (3aR,4S,5S,6aS)-4-diphenylphosphanyl-3-[(diphenylphosphanyl)methyl]-2-(2-hydroxyethyl)cyclopentanol-borane complex (Compound 4, 2.2 g, yield: 86%).

$^1$H NMR (CDCl$_3$, 300 MHz): δ 7.89-7.11 (m, 20H), 4.27 (s, 1H), 3.59-3.46 (m, 2H), 3.2-3.22 (m, 1H), 2.64 (t, J=13.8 Hz, 1H), 2.41-2.26 (m, 3H), 2.05 (brs, 1H), 1.81 (m, 1H), 1.68-1.57 (m, 1H), 1.45-1.41 (m, 1H), 1.03 (brs, 6H)

[α]$_D^{20}$=+17.94 (c=1.01, toluene)

Example 4

Preparation of (3aS,4R,5R,6aR)-5-diphenylphosphanyl-4-[(diphenylphosphanyl)methyl]hexahydrocyclopenta[b]furan-borane complex (Compound 5)

To a 25 mL three-neck flask attached with a three-way cock were added pyridine (0.17 mL, 2.06 mmol) and 4 mL of dichloromethane, and the reaction mixture was cooled. To the flask were added p-toluenesulfonic acid anhydride (336 mg, 1.03 mmol) and a solution of (3aS,4R,5R,6aR)-4-diphenylphosphanyl-3-[(diphenylphosphanyl)methyl]-2-(2-hydroxyethyl)cyclopentanol-borane complex (enantiomer of Compound 4) in 2 mL of dichloromethane, and the mixture was stirred for 4 hours. The reaction mixture was stirred at room temperature for 14 hours, then cooled, and added with 5 mL of water, and the mixture was stirred for 30 minutes. The reaction mixture was transferred to a separatory funnel, and extracted three times with 5 mL of toluene. The organic layers were combined, and washed five times with 5 mL of diluted hydrochloric acid and then with 5 mL of saturated brine. The organic layer was dried over anhydrous magnesium sulfate, and after the drying agent was removed by filtration, concentrated in an evaporator. The residue was purified by silica gel column chromatography (toluene:ethyl acetate=12:1) to obtain (3aS,4R,5R,6aR)-5-diphenylphosphanyl-4-[(diphenylphosphanyl)methyl]-hexahydrocyclopenta[b]furan-borane complex (Compound 5, 140 mg, yield: 65%).

$^1$H NMR (CDCl$_3$, 300 MHz): δ 7.77-7.10 (m, 20H), 4.39-4.32 (m, 1H), 3.87-3.80 (m, 1H), 3.39-3.31 (m, 1H), 3.29-3.18 (m, 1H), 3.02-2.92 (m, 2H), 2.39-2.05 (m, 4H), 1.86 (dd, J=5.4, 15.0 Hz, 1H), 1.50-1.37 (m, 1H), 1.20 (brs, 6H)

[α]$_D^{20}$=+32.15 (c=1.03, toluene)

Example 5

Preparation of (3aR,4S,5S,6aS)-4-diphenylphosphanyl-3-[(diphenylphosphanyl)methyl]-2-(2-triphenylmethyloxyethyl)cyclopentanol-borane complex (Compound 6)

To a 25 mL-recovery flask were added (3aR,4S,5S,6aS)-4-diphenylphosphanyl-3-[(diphenylphosphanyl)methyl]-2-(2-hydroxyethyl)cyclopentanol-borane complex (Compound 4, 0.54 g, 1.0 mmol), 5 mL of dichloromethane, and triethylamine (0.18 mL, 1.3 mmol), and the mixture was stirred with cooling for dissolution. The solution was added dropwise with a solution of triphenylmethane chloride (0.42 g, 1.5 mol) in 2 mL of dichloromethane. The reaction mixture was stirred at room temperature for 16 hours, then cooled, and added with 20 mL of toluene and 10 mL of water. The reaction mixture was transferred to a separatory funnel to separate the layers, and the aqueous layer was extracted three times with 5 mL of toluene. Then, the organic layers were combined, and washed three times with 5 mL of saturated brine. The organic layer was dried over anhydrous magnesium sulfate, and after the drying agent was removed by filtration, concentrated in an evaporator to obtain (3aR,4S,5S,6aS)-4-diphenylphosphanyl-3-[(diphenylphosphanyl)methyl]-2-(2-triphenylmethyloxyethyl)cyclopentanol-borane complex (Compound 6, 0.9 g). This compound was used in the following step without purification.

$^1$H NMR (CDCl$_3$, 300 MHz): δ 7.89-7.06 (m, 35H), 4.18 (brs, 1H), 3.61-3.47 (m, 1H), 3.41 (brs, 1H), 3.11-3.08 (m, 1H), 2.57-2.19 (m, 4H), 1.89-1.39 (m, 4H), 0.94 (brs, 6H)

[α]$_D^{20}$=−4.96 (c=0.99, toluene)

Example 6

Preparation of (3aR,4S,5S,6aS)-4-diphenylphosphanyl-3-[(diphenylphosphanyl)methyl]-2-(2-triphenylmethyloxyethyl)-1-methoxycyclopentane-borane complex (Compound 7)

To a 25 mL-recovery flask were added sodium hydride (30.9 mg, 0.77 mmol) and 2 mL of dimethylformamide, and the mixture was cooled on an ice bath. The mixture was added dropwise with a solution of (3aR,4S,5S,6aS)-4-diphenylphosphanyl-3-[(diphenylphosphanyl)methyl]-2-(2-triphenylmethyloxyethyl)cyclopentanol-borane complex (Compound 6, 0.52 g, 0.55 mmol) in 4 mL of dimethylformamide, and the mixture was stirred at room temperature for 30 minutes, and then added dropwise with methyl iodide (0.17 mL, 1.3 mmol). The mixture was stirred overnight, then cooled, and added with 10 mL of toluene and 3 mL of water. The reaction mixture was transferred to a separatory funnel to separate the layers, the aqueous layer was extracted twice with 3 mL of toluene, and the organic layers were combined and washed twice with 5 mL of saturated brine. The organic layer was dried over anhydrous magnesium sulfate, and after the drying agent was removed by filtration, concentrated in an evaporator. The residue was purified by silica gel column chromatography (toluene) to obtain (3aR,4S,5S,6aS)-4-diphenylphosphanyl-3-[(diphenylphosphanyl)methyl]-2-(2-trityloxyethyl)-1-methoxycyclopentane-borane complex (Compound 7, 0.19 g, yield: 43% from (3aR,4S,5S,6aS)-3,4-diphenylphosphanyl-3-[(diphenylphosphanyl)methyl]-2-(2-hydroxyethyl)cyclopentanol-borane complex).

$^1$H NMR (CDCl$_3$, 300 MHz): δ 7.84-7.07 (m, 35H), 3.49-3.32 (m, 2H), 2.87-2.74 (m, 1H), 2.82 (s, 3H), 2.67-2.29 (m, 4H), 2.23-2.09 (m, 1H), 1.95-1.88 (m, 1H), 1.71-1.54 (m, 2H), 1.46-1.31 (m, 1H), 1.05 (brs, 6H)

[α]$_D^{20}$=+30.16 (c=1.14, toluene)

Example 7

Preparation of (5aR,6S,7S,8aS)-7-diphenylphosphanyl-6-[(diphenylphosphanyl)methyl]-2,2-dimethylhexahydrocyclopenta[d][1,3]dioxepine-borane complex (Compound 8)

To a 30 mL-two-neck flask were added (3aR,4S,5S,6aS)-4-diphenylphosphanyl-3-[(diphenylphosphanyl)methyl]-2-(2-hydroxyethyl)cyclopentanol-borane complex (Compound 4, 0.54 g, 1.0 mmol), 10 mL of 2,2-dimethoxypropane and about 10 mg of p-toluenesulfonic acid monohydrate, and the mixture was stirred at 50° C. for 3 hours. The reaction mixture was cooled to room temperature, and the solvent was concentrated in an evaporator. The residue was purified by silica gel column chromatography (toluene) to obtain (5aR,6S,7S,8aS)-7-diphenylphosphanyl-6-[(diphenylphosphanyl)methyl]-2,2-dimethylhexahydrocyclopenta[d][1,3]dioxepine-borane complex (Compound 8, 0.27 g, yield: 47%).

¹H NMR (CDCl₃, 300 MHz): δ 7.89-7.13 (m, 20H), 4.42 (t, J=6.2 Hz, 1H), 3.74-3.66 (m, 1H), 3.37-3.23 (m, 2H), 2.50-2.21 (m, 5H), 1.96-1.70 (m, 2H), 1.46-1.34 (m, 1H), 1.28 (s, 3H), 1.19 (s, 3H)

$[\alpha]_D^{20}$=−2.32 (c=1.01, toluene)

Example 8

Preparation of (3aR,4S,5S,6aS)-5-di(4-methoxy-3,5-dimethylphenyl)phosphanyl]-4-[(di(4-methoxy-3,5-dimethylphenylphosphanyl)methyl]hexahydrocyclopenta[b]furan-2-one-borane complex (Compound 9)

To a 30 mL-two-neck flask were added di(4-methoxy-3,5-dimethylphenyl)phosphine-borane complex (0.52 g, 1.7 mmol) and 4 mL of dehydrated THF, and the mixture was cooled to −15° C., and slowly added dropwise with a 1.54 mol/L solution of n-butyllithium (1.1 mL, 1.7 mmol) in hexane. The mixture was stirred for 10 minutes, and then added dropwise with a solution of (3aR,4S,5R,6aS)-5-p-toluenesulfoxy-4-[(p-toluenesulfoxy)methyl]hexahydrocyclopenta[b]furan-2-one (Compound 2, 0.33 g, 0.7 mmol) in 4 mL of tetrahydrofuran, and the mixture was stirred at room temperature for 16 hours. The reaction mixture was added with 40 mL of diethyl ether and 20 mL of saturated brine, the layers were separated, and the aqueous layer was extracted twice with 20 mL of diethyl ether. The organic layers were combined, and washed twice with 10 mL of saturated brine. The organic layer was dried over anhydrous magnesium sulfate, and after the drying agent was removed by filtration, concentrated in an evaporator. The residue was purified by silica gel column chromatography (toluene:ethyl acetate=10:1) to obtain (3aR,4S,5S,6aS)-5-di(4-methoxy-3,5-dimethylphenyl)phosphanyl]-4-[(di(4-methoxy-3,5-dimethylphenyl)phosphanyl)methyl]hexahydrocyclopenta[b]furan-2-one-borane complex (Compound 9, 0.10 g, yield: 19%).

¹H NMR (CDCl₃, 300 MHz): δ 7.37-7.23 (m, 6H), 7.00 (d, J=10.5 Hz, 2H), 4.94 (t, J=5.9 Hz, 1H), 3.73 (s, 3H), 3.71 (s, 3H), 3.69 (s, 3H), 3.68 (s, 3H), 3.15-3.02 (m, 1H), 2.92-2.88 (m, 1H), 2.71-2.04 (m, 7H), 2.29 (s, 6H), 2.25 (s, 6H), 2.22 (s, 6H), 2.17 (s, 6H), 1.15 (brs, 6H)

$[\alpha]_D^{20}$=−38.66 (c=1.03, toluene)

Example 9

Preparation of (3aR,4S,5S,6aS)-(5-diphenylphosphanyl-4-[(diphenylphosphanyl)methyl]hexahydrocyclopenta[b]furan-2-one (CLPL-S)

To a 25 mL-recovery flask were added (3aR,4S,5S,6aS)-(5-diphenylphosphanyl-4-[(diphenylphosphanyl)methyl]hexahydrocyclopenta[b]furan-2-one-borane complex (Compound 3, 1.0 mmol) and 1,4-diazobicyclo[2,2,2]octane (DABCO, 0.25 g, 2.2 mmol), and the atmosphere in the flask was substituted with nitrogen. The mixture was added with 10 mL of deoxygenized toluene, and stirred at 40° C. for 3 hours. The solvent was concentrated in an evaporator, and the residue was purified by silica gel column chromatography (toluene/ethyl acetate=20/1 to 4/1) to obtain (3aR,4S,5S,6aS)-(5-diphenylphosphanyl-4-[(diphenylphosphanyl)methyl]hexahydrocyclopenta[b]furan-2-one (CLPL-S, yield: 85%).

¹H NMR (CDCl₃, 300 MHz): δ 7.45-7.01 (m, 20H), 5.07 (t, J=5.7 Hz, 1H), 3.35 (brs, 1H), 3.03-2.94 (m, 1H), 2.89 (dd, J=10.6, 18.7 Hz, 1H), 2.72-2.66 (m, 1H), 2.23 (dd, J=3, 2, 18.8 Hz, 1H), 2.15-2.01 (m, 1H), 1.97-1.79 (m, 3H)

$[\alpha]_D^{20}$=−139.57 (c=1.01, toluene)

Example 10

Preparation of (3aR,4S,5S,6aS)-4-diphenylphosphanyl-3-[(diphenylphosphanyl)methyl]-2-(2-hydroxyethyl)cyclopentanol (CLPDO-S)

The target compound was obtained from (3aR,4S,5S,6aS)-4-diphenylphosphanyl-3-[(diphenylphosphanyl)methyl]-2-(2-hydroxyethyl)cyclopentanol-borane complex (Compound 4) in the same manner as that of Example 9 at a yield of 84%.

¹H NMR (CDCl₃, 300 MHz): δ 7.59-7.53 (m, 2H), 7.46-7.08 (m, 16H), 7.02-6.97 (m, 2H), 4.35 (t, J=4.8 Hz, 1H), 3.80-3.74 (m, 1H), 3.67-3.60 (m, 1H), 3.33-3.23 (m, 1H), 2.69-2.63 (m, 1H), 2.30-2.21 (m, 1H), 2.05-1.76 (m, 5H), 2.00 (brs, 2H), 1.62 (dd, J=6.0, 12.0 Hz, 1H)

$[\alpha]_D^{20}$=−74.45 (c=1.00, toluene)

Example 11

Preparation of (3aR,4S,5S,6aS)-4-diphenylphosphanyl-3-[(diphenylphosphanyl)methyl]-2-(2-triphenylmethyloxyethyl)cyclopentanol (CLPTO-S)

The target compound was obtained from (3aR,4S,5S,6aS)-4-diphenylphosphanyl-3-[(diphenylphosphanyl)methyl]-2-(2-triphenylmethyloxyethyl)cyclopentanol-borane complex (Compound 6) in the same manner as that of Example 9 at a yield of 87%.

¹H NMR (CDCl₃, 300 MHz): δ 7.58-7.52 (m, 2H), 7.43-7.06 (m, 41H), 6.97-6.92 (m, 2H), 4.19 (brs, 1H), 3.45-3.40 (m, 1H), 3.35-3.28 (m, 2H), 3.05-3.00 (m, 1H), 2.61 (dd, J=5.3, 10.4 Hz, 1H), 2.09-1.80 (m, 6H), 1.63 (dd, J=6.2, 13.1 Hz, 1H)

$[\alpha]_D^{20}$=−45.41 (c=1.02, toluene)

Example 12

Preparation of (3aR,4S,5S,6aS)-4-diphenylphosphanyl-3-[(diphenylphosphanyl)methyl]-2-(2-triphenylmethyloxyethyl)-1-methoxycyclopentane (CLPTM-S)

The target compound was obtained from (3aR,4S,5S,6aS)-4-diphenylphosphanyl-3-[(diphenylphosphanyl)methyl]-2-(2-trityloxyethyl)-1-methoxycyclopentane-borane complex (Compound 7) in the same manner as that of Example 9 at a yield of 87%.

¹H NMR (CDCl₃, 300 MHz): δ 7.47-6.98 (m, 35H), 3.50 (brs, 1H), 3.12 (m, 2H), 2.90 (s, 3H), 2.90 (m, 1H), 2.60-2.57 (m, 1H), 2.35 (m, 1H), 1.99-1.54 (m, 6H)

$[\alpha]_D^{20}$=−16.31 (c=0.98, toluene)

Example 13

Preparation of (3aS,4R,5R,6aR)-5-diphenylphosphanyl-4-[(diphenylphosphanyl)methyl]hexahydrocyclopenta[b]furan (CLPF-R)

The target compound was obtained from (3aS,4R,5R,6aR)-5-diphenylphosphanyl-4-[(diphenylphosphanyl)methyl]hexahydrocyclopenta[b]furan-borane complex (Compound 5) in the same manner as that of Example 9 at a yield of 100%.

¹H NMR (CDCl₃, 300 MHz): δ 7.47-7.06 (m, 20H), 4.45 (t, J=6.2 Hz, 1H), 3.90-3.84 (m, 1H), 3.53-3.45 (m, 1H), 3.16-

2.98 (m, 2H), 2.72-2.66 (m, 1H), 2.23-2.14 (m, 1H), 2.04-1.72 (m, 4H), 1.53-1.42 (m, 1H)

$[\alpha]_D^{20}$=+117.83 (c=1.00, toluene)

Example 14

Preparation of (3aR,4S,5S,6aS)-7-diphenylphosphanyl-6-[(diphenylphosphanyl)methyl]-2,2-dimethyl-hexahydrocyclopenta[d][1,3]dioxepine (CLPOX-S)

The Target Compound was Obtained from (3Ar,4S,5S,6as)-7-diphenylphosphanyl-6-[(diphenylphosphanyl)methyl]-2,2-dimethylhexahydrocyclopenta[d][1,3]dioxepine-borane complex (Compound 8) in the same manner as that of Example 9 at a yield of 79%.

$^1$H NMR (CDCl$_3$, 300 MHz): δ 7.37-7.13 (m, 6H), 7.00 (d, J=10.5 Hz, 2H), 4.94 (t, J=5.9 Hz, 1H), 3.73 (s, 3H), 3.71 (s, 3H), 3.69 (s, 3H), 3.68 (s, 3H), 3.15-3.02 (m, 1H), 2.92-2.88 (m, 1H), 2.71-2.04 (m, 7H), 2.29 (s, 3H), 2.25 (s, 3H), 2.22 (s, 3H), 2.17 (s, 3H), 1.15 (brs, 6H)

$[\alpha]_D^{20}$=−79.72 (c=1.20, toluene)

Example 15

Preparation of (3aR,4S,5S,6aS)-5-di(4-methoxy-3,5-dimethylphenyl)phosphanyl]-4-[(di(4-methoxy-3,5-dimethylphenylphosphanylmethyl]hexahydrocyclopenta[b]furan-2-one-borane (CLMPL-S)

The target compound was obtained from (3aR,4S,5S,6aS)-5-di(4-methoxy-3,5-dimethylphenyl)phosphanyl]-4-[(di(4-methoxy-3,5-dimethylphenyl)phosphanylmethyl]hexahydrocyclopenta[b]furan-2-one-borane complex (Compound 9) in the same manner as that of Example 9 at a yield of 76%.

$^1$H NMR (CDCl$_3$, 300 MHz): δ 7.08-6.94 (m, 6H), 6.82 (d, J=7.8 Hz, 2H), 4.99 (t, J=6.0 Hz, 1H), 3.70 (s, 3H), 3.69 (s, 3H), 3.68 (s, 3H), 3.67 (s, 3H), 3.31 (brs, 1H), 2.91-2.81 (m, 2H), 2.67-2.63 (m, 1H), 2.44-1.68 (m, 3H), 2.24 (s, 6H), 2.21 (s, 12H), 2.07 (s, 6H)

$[\alpha]_D^{20}$=−104.76 (c=1.03, toluene)

Example 16

Preparation of [Rh(CLPL-S)(COD)]BF$_4$ (COD=1,5-cyclooctadiene)

To a 10 mL-recovery flask were added [RhCl(COD)]$_2$ (0.12 g, 0.23 mmol) and silver tetrafluoroborate (0.1 g, 0.49 mmol), and the atmosphere in the flask was substituted with nitrogen. The mixture was added with 1 mL of acetone, stirred for 15 minutes, then added with a solution of CLPL-S (0.47 mmol) in 3 mL of acetone, and stirred for 30 minutes. The precipitated solid was collected by filtration, and then the filtrate was evaporated under reduced pressure until the remaining volume became about 1 mL. The remaining filtrate was added with 30 mL of dehydrated diethyl ether to cause crystallization, and the precipitated solid was collected by filtration and dried to obtain the metal complex as orange solid (yield: 99%).

$^{31}$PNMR (160 MHz, acetone-d$_6$): δ 26.5 (dd, 46.9, 143.9 Hz), 20.2 (dd, 46.9, 145.5 Hz)

Example 17

Preparation of [Rh(CLPDO-S)(COD)]BF$_4$

The target compound was obtained in the same manner as that of Example 16 except that CLPD was used instead of CLPL-S (yield: 93%). $^{31}$PNMR (160 MHz, acetone-d$_6$): δ 30.5(dd, 46.7, 141.5 Hz), 20.1 (dd, 46.7, 142.8 Hz)

Example 18

Preparation of [Rh(CLPTO-S)(COD)]BF$_4$

The target compound was obtained in the same manner as that of Example 16 except that CLPTO-S was used instead of CLPL-S (yield: 76%).

$^{31}$PNMR (160 MHz, acetone-d$_6$): δ 30.6(dd, 46.9, 142.3 Hz), 20.2 (dd, 46.9, 143.9 Hz)

Example 19

Preparation of [Rh(CLPTM-S)(COD)]BF$_4$

The target compound was obtained in the same manner as that of Example 16 except that CLPTM-S was used instead of CLPL-S (yield: 67%).

$^{31}$PNMR (160 MHz, acetone-d$_6$): δ 31.0(ddd, 22.0, 46.7, 142.9 Hz), 20.3 (ddd, 23.3, 46.7, 142.8 Hz)

Example 20

Preparation of [Rh(CLPOX-S)(COD)]BF$_4$

The target compound was obtained in the same manner as that of Example 16 except that CLPOX-S was used instead of CLPL-S (yield: 82%).

$^{31}$PNMR (160 MHz, acetone-d$_6$): δ 30.6(dd, 45.9, 141.5 Hz), 20.2 (dd, 46.0, 142.8 Hz)

Example 21

Preparation of [Rh(CLPF-R)(COD)]BF$_4$

The target compound was obtained in the same manner as that of Example 16 except that CLPF-R was used instead of CLPL-S (yield: 89%).

$^{31}$PNMR (160 MHz, acetone-d$_6$): δ 26.3(dd, 46.6, 142.8 Hz), 19.9 (dd, 45.4, 144.2 Hz)

Example 22

Preparation of [Rh(CLMPL-S)(COD)]BF$_4$

The target compound was obtained in the same manner as that of Example 16 except that CLMPL-S was used instead of CLPL-S (yield: 72%).

Example 23

Preparation of Optically Active N-acetylphenylalanine Using Rhodium Metal Complex Catalyst

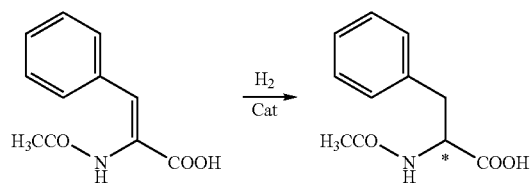

The atmosphere in a 25 mL-recovery flask was substituted with nitrogen, and 3 mL of deoxygenized methanol and triethylamine (20.9 μL, 0.15 mmol) were added to the flask as the reaction solvent. α-Acetamidocinnamic acid (0.20 g, 0.98 mmol) and [Rh(CLPL-S)(COD)]BF$_4$ (3.95 mg, 0.0049 mmol) were weighed in a 50 mL-Pyrex (registered trade name) test tube for autoclaving, the tube was put into an autoclave together with a stirrer in the tube, and the atmosphere in the autoclave was substituted with nitrogen. The reaction solvent in a volume of 2 mL was added to the mixture, the atmosphere in the autoclave was sufficiently substituted with hydrogen, and then pressurized with 2 MPa of hydrogen, and the reaction mixture was stirred at 40° C. for 22 hours. After 22 hours, the atmosphere in the autoclave was returned to ordinary pressure, and the reaction mixture was concentrated in an evaporator. The concentrated residue was added with 5 mL of 2 M aqueous sodium hydroxide for dissolution, and the solution was washed with 5 mL of ethyl acetate. The aqueous layer was separated, and added with diluted hydrochloric acid until pH of the aqueous layer became lower than 2, and the produced oil was extracted with 10 mL of ethyl acetate. The organic layer was concentrated in an evaporator to obtain (R)-N-acetylphenylalanine quantitatively.

$^1$H NMR (300 MHz, CD$_3$OD): δ 7.25-7.12 (m, 5H), 4.58 (dd, J=4.8, 8.9 Hz, 1H), 3.15 (dd, J=5.1, 13.8 Hz, 1H), 2.89 (dd, J=9.0, 13.8 Hz, 1H), 1.89 (s, 3H)

The resulting (R)-N-acetylphenylalanine in an amount of 2 mg was dissolved in 0.5 mL of methanol and 0.5 mL of dichloromethane, and the solution was added with a 10% solution of trimethylsilyldiazomethane in n-hexane until the solution colored in yellow to obtain the methyl ester compound. The solvent was concentrated in an evaporator, and the residue was dissolved in 1 mL of a mixture of n-hexane and 2-propanol (9:1). HPLC analysis of this solution under the following conditions revealed that the compound consist of 95% ee of the (R)-isomer.

Analysis conditions: Chiralcel-OD produced by Daicel Chemical Industries, Ltd., mobile phase: n-hexane/2-propanol=9/1, flow rate: 1.0 mL/min., detector wavelength: 220 nm, column temperature: 40° C., injection: 2 μL, R.T.: R-isomer=8.4 min., S-isomer=9.8 min.

Examples 24 to 28

Preparation of Optically Active N-acetylphenylalanine Using Rhodium Metal Complex Catalyst The target compounds were synthesized in the same manner as that of Example 23 except for the metal complex catalyst.

TABLE 1

| Example | Metal complex catalyst | Steric configuration | % ee |
|---|---|---|---|
| 24 | [Rh(CLPDO-S)(COD)]BF$_4$ | (R) | 87 |
| 25 | [Rh(CLPTO-S)(COD)]BF$_4$ | (R) | 85 |
| 26 | [Rh(CLPTM-S)(COD)]BF$_4$ | (R) | 85 |
| 27 | [Rh(CLPOX-S)(COD)]BF$_4$ | (R) | 83 |
| 28 | [Rh(CLMPL-S)(COD)]BF$_4$ | (R) | 95 |

Examples 29 to 30

Preparation of Optically Active N-acetylphenylalanine Using Rhodium Metal Complex Catalyst α-Acetamidocinnamic acid (0.20 g, 0.98 mmol), [RhCl(COD)]$_2$ (1.2 mg, 0.0025 mmol) and a ligand (0.005 mmol) were weighed in a 50 mL-Pyrex (registered trade name) test tube for autoclaving, and a stirrer was put into the tube. This test tube was set in a 50 mL-autoclave, and the atmosphere in the autoclave was substituted three times with nitrogen. The reaction mixture was added with 2 mL of degassed methanol, the atmosphere in the autoclave was sufficiently substituted with hydrogen, and then pressurized with 0.8 MPa of hydrogen, and the reaction mixture was stirred at 40° C. for 22 hours. The post-treatment after the reaction was performed in the same manner as that of Example 23.

TABLE 2

| Example | Ligand | Steric configuration | % ee |
|---|---|---|---|
| 29 | CLPDO-S | (R) | 87 |
| 30 | CLPF-R | (S) | 98 |

Examples 31 to 36

Preparation of Optically Active 3-methoxycarbonyl-4-cyclohexylbutyric Acid Using Rhodium Metal Complex Catalyst

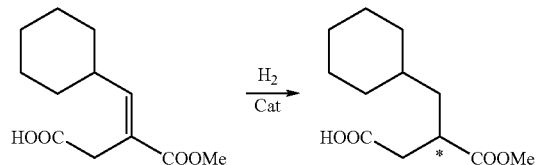

2-Cyclohexylmethylidenesuccinic acid 1-methyl ester (0.22 g, 1.0 mmol) and each metal complex catalyst (0.005 mmol) were weighed in a Pyrex (registered trade name) test tube for autoclaving and the tube was put into a 50 mL-autoclave together with a stirrer in the tube, and then the atmosphere in the autoclave was substituted with nitrogen. The mixture was added with 2 mL of deoxygenized methanol, and after the atmosphere in the autoclave was sufficiently substituted with hydrogen, and then pressurized with 0.5 MPa of hydrogen, the mixture was stirred at 45° C. for 18 hours. After 18 hours, the atmosphere of the autoclave was returned to ordinary pressure, and the reaction mixture was concentrated in an evaporator. The concentrated residue was added with 5 mL of 2 M aqueous sodium hydroxide for dissolution, and the solution was washed with 5 mL of ethyl acetate. The aqueous layer was separated, and added with diluted hydrochloric acid until pH of the aqueous layer became lower than 2, and the produced oil was extracted with 10 mL of ethyl acetate. The organic layer was concentrated in an evaporator to quantitatively obtain optically active cyclohexylmethylsuccinic acid 1-methyl ester.

$^1$H NMR (300 MHz, CDCl$_3$): δ 3.70 (s, 3H), 2.97-2.87 (m, 1H), 2.73 (dd, J=9.5, 16.8 Hz, 1H), 2.47 (dd, J=4.8, 16.8 Hz, 1H), 1.79-1.53 (m, 6H), 1.44-1.07 (m, 5H), 0.95-0.82 (m, 2H)

The resulting optically active 3-methoxycarbonyl-4-cyclohexylbutyric acid in an amount of 9.5 mg was dissolved in 5 mL of benzene, and added with 27 µL of trifluoroacetic acid anhydride, and the mixture was stirred at 40° C. for 1 hour. The reaction mixture was added with 0.88 mL of a 213 mM solution of phenol in benzene, and the mixture was further stirred for 20 minutes. The reaction mixture was transferred to a separatory funnel, washed with 5 mL of 2 M aqueous sodium hydroxide, and dried over anhydrous sodium sulfate. After the drying agent was removed by filtration, the reaction mixture was concentrated in an evaporator, and the residue was dissolved in 1 mL of a mixture of n-hexane and 2-propanol (99:1).

Analysis conditions: Chiralcel-OD produced by Daicel Chemical Industries, Ltd., mobile phase: n-hexane/2-propanol=99/1, flow rate: 1.0 mL/min., detector wavelength: 254 nm, column temperature: 40° C., injection: 2 µL, R.T.: S-isomer=11.9 min., R-isomer=29.2 min.

TABLE 3

| Example | Metal complex catalyst | Steric configuration | % ee |
|---|---|---|---|
| 31 | [Rh(CLPL-S)(COD)]BF$_4$ | (R) | 87 |
| 32 | [Rh(CLPDO-S)(COD)]BF$_4$ | (R) | 96 |
| 33 | [Rh(CLPTO-S)(COD)]BF$_4$ | (R) | 96 |
| 34 | [Rh(CLPTM-S)(COD)]BF$_4$ | (R) | 95 |
| 35 | [Rh(CLPOX-S)(COD)]BF$_4$ | (R) | 95 |
| 36 | [Rh(CLPF-R) (COD)]BF$_4$ | (S) | 87 |

Examples 37 to 38

Preparation of Optically Active 3-methoxycarbonyl-5-methylcaproic Acid Using Rhodium Metal Complex Catalyst

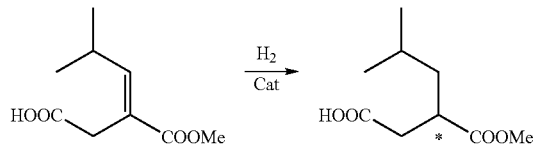

The preparation was performed in the same manner as those of Example 31 to 36 except that isobutylidenesuccinic acid 1-methyl ester was used as the substrate.

3-Methoxycarbonyl-5-methylcaproic acid $^1$H NMR (300 MHz, CDCl$_3$): δ 3.66 (s, 3H), 2.90-2.81 (m, 1H), 2.60 (dd, J=9.3, 16.8 Hz, 1H), 2.47 (dd, J=5.3, 16.8 Hz, 1H), 1.62-1.48 (m, 2H), 1.36-1.26 (m, 1H), 0.91 (dd, J=6.6, 11.1 Hz, 6H)

The resulting optically active 3-methoxycarbonyl-5-methylcaproic acid in an amount of 10 mg was dissolved in 0.5 mL of methanol and 0.5 mL of dichloromethane, and the solution was added with a 10% solution of trimethylsilyldiazomethane in n-hexane until the solution colored in yellow to obtain the methyl ester compound. The solvent was concentrated in an evaporator, and the residue was dissolved in 1 mL of a mixture of n-hexane and 2-propanol (99.5:0.5). This solution was analyzed by HPLC under the following conditions.

Analysis conditions: Chiralcel-OD produced by Daicel Chemical Industries, Ltd., mobile phase: n-hexane/2-propanol=99.5/0.5, flow rate: 1.0 mL/min., detector wavelength: 220 nm, column temperature: 40° C., injection: 2 µL, R.T.: S-isomer=8.9 min., R-isomer=21.0 min.

TABLE 4

| Example | Metal complex catalyst | Steric configuration | % ee |
|---|---|---|---|
| 37 | [Rh(CLPL-S)(COD)]BF$_4$ | (R) | 85 |
| 38 | [Rh(CLPDO-S)(COD)]BF$_4$ | (R) | 96 |

Examples 39 to 42

Preparation of Optically Active 3-methoxycarbonyl-5-phenylvaleric Acid Using Rhodium Metal Complex Catalyst

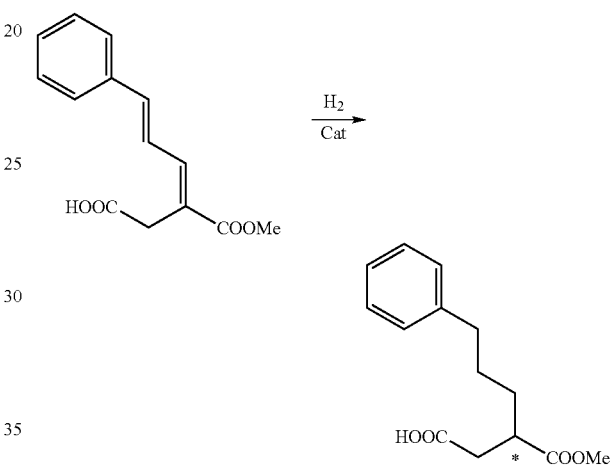

The preparation was performed in the same manner as those of Examples 21 to 26 except that cinnamilidenesuccinic acid 1-methyl ester was used as the substrate.

3-Methoxycarbonyl-5-phenylvaleric acid $^1$H NMR (300 MHz, CDCl$_3$): δ 7.30-7.14 (m, 5H), 3.72 (s, 3H), 2.88-2.82 (m, 1H), 2.76 (dd, J=9.3, 16.5 Hz, 1H), 2.61 (t, 7.1 Hz, 2H), 2.46 (dd, J=4.5, 16.5 Hz, 1H), 1.73-1.54 (m, 4H)

The resulting optically active 3-methoxycarbonyl-5-phenylvaleric acid in an amount of 2 mg was dissolved in 0.5 mL of methanol and 0.5 mL of dichloromethane, and added with a 10% solution of trimethylsilyldiazomethane in n-hexane until the solution colored in yellow to prepare the methyl ester compound. The solvent was concentrated in an evaporator, and the residue was dissolved in 1 mL of a mixture of n-hexane and 2-propanol (95:5). This solution was analyzed by HPLC under the following conditions.

Analysis conditions: Chiralcel-OD produced by Daicel Chemical Industries, Ltd., mobile phase: n-hexane/2-propanol=95/5, flow rate: 1.0 mL/min., detector wavelength: 220 nm, column temperature: 40° C., injection: 2 µL, R.T.: S-isomer=6.8 min., R-isomer=9.0 mm.

TABLE 5

| Example | Metal complex catalyst | Steric configuration | % ee |
|---|---|---|---|
| 39 | [Rh(CLPDO-S)(COD)]BF$_4$ | (R) | 82 |
| 40 | [Rh(CLPTO-S)(COD)]BF$_4$ | (R) | 76 |

TABLE 5-continued

| Example | Metal complex catalyst | Steric configuration | % ee |
|---|---|---|---|
| 41 | [Rh(CLPTM-S)(COD)]BF$_4$ | (R) | 72 |
| 42 | [Rh(CLPOX-S)(COD)]BF$_4$ | (R) | 80 |

Examples 43 to 45

Preparation of Optically Active 3-phenylcyclohexanone Using Rhodium Metal Complex Catalyst

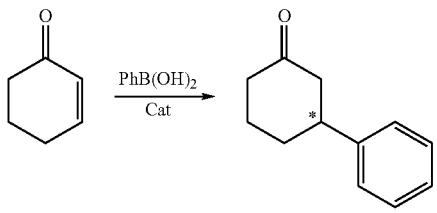

To a 25-mL three-neck flask were added Rh(acac)(cod) (6.8 mg, 21.8 μmol) and PhB(OH)$_2$ (445 mg, 3.65 mmol), and the atmosphere in the system was substituted with argon. The mixture was added with 3.6 mL of a solution of each ligand (21.8 μmol) in anhydrous dioxane and 2-cyclohexenone (0.073 mL, 0.73 mmol). The mixture was stirred at room temperature for 15 minutes, and added with water (0.18 mL). The reaction mixture was stirred at 100° C. for 3 hours, then added with 9 mL of water, and extracted twice with 9 mL of diethyl ether. The organic layers were combined, washed with 9 mL of saturated sodium chloride solution, and concentrated in an evaporator. The residue was treated by silica gel column chromatography (toluene:ethyl acetate=2:1) to obtain 3-phenylcyclohexane as colorless oil. The resulting optically active 3-phenylcyclohexanone in an amount of 2 mg was dissolved in 1 mL of a mixture of n-heptane and 2-propanol (99:2). This solution was analyzed by HPLC under the following conditions.

Analysis conditions: Chiralcel-ODH produced by Daicel Chemical Industries, Ltd., mobile phase: n-heptane: 2-propanol=99:2, flow rate: 1.0 mL/min., detector wavelength: 215 nm, column temperature: 40° C., injection: 2 μL, R.T.: S-isomer=36.7 min., R-isomer=39.6 min.

TABLE 6

| Example | Ligand | Steric configuration | % ee |
|---|---|---|---|
| 43 | CLPL-S | (S) | 5 |
| 44 | CLPF-R | (R) | 31 |
| 45 | CLPDO-S | (S) | 23 |

Examples 46 to 48

Preparation of Optically Active 2-benzylamino-1-(4-fuluorophenyl)ethanol Using Rhodium Metal Complex Catalyst

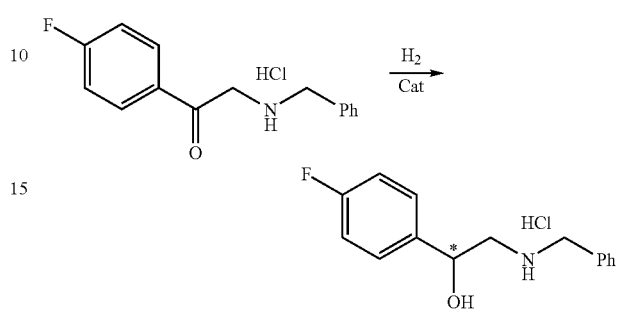

In a 25 mL-recovery flask, each ligand (0.050 mmol) and [RhCl(COD)]$_2$ (11.2 mg, 0.227 mmol) were weighed, and the atmosphere in the flask was substituted with argon. The mixture was added with 20 mL of degassed methanol and triethylamine (0.13 mL, 0.91 mmol) and made into a solution by dissolution to prepare a catalyst solution. Separately, 2-benzylamino-1-(4-fuluorophenyl)ethanone hydrochloride (254 mg, 0.908 mmol) was weighed in a Pyrex (registered trade name) test tube for autoclaving, the test tube was set in a 50-mL autoclave together with a stirrer in the tube, and the atmosphere in the autoclave was substituted with nitrogen five times. The reaction mixture was added with 2 mL of the prepared catalyst solution (corresponding to 0.00454 mmol of catalyst), the atmosphere in the autoclave was sufficiently substituted with hydrogen, and then pressurized with 1.5 MPa of hydrogen, and the reaction was allowed at 50° C. for 22 hours. The solvent of the reaction mixture was evaporated, and the residue was transferred to a separatory funnel with dissolving it in 20 mL of water and 10 mL of toluene, and the aqueous layer was separated. pH of the aqueous layer was made higher than 11 with 2 M aqueous sodium hydroxide, and the produced oil was extracted with 10 mL of ethyl acetate. The organic layer was concentrated in an evaporator to quantitatively obtain optically active 2-benzylamino-1-(4-fuluorophenyl)ethanol.

$^1$H NMR (300 MHz, CD$_3$OD): δ 7.53-7.40 (m, 7H), 7.14-7.07 (m, 2H), 4.98 (dd, 3.3, 10.2 Hz, 1H), 4.27 (s, 3H), 3.22-3.03 (m, 2H)

The resulting optically active 2-benzylamino-1-(4-fuluorophenyl)ethanol weighed in an amount of 2 mg was dissolved in 1 mL of a mixture of n-hexane: 2-propanol:diethylamine=98:2:0.1, and HPLC was performed under the following conditions.

Analysis conditions: CHIRALPAK AS-H produced by Daicel Chemical Industries, Ltd., n-hexane: 2-propanol:diethyl amine=98:2:0.1, flow rate: 1.0 mL/min., detector wavelength: 265 nm, column temperature: 35° C., injection: 2 μL, R.T.: S-isomer=21.1 min., R-isomer=25.3 min.

TABLE 7

| Example | Ligand | Steric configuration | % ee |
|---|---|---|---|
| 46 | CLPL-S | (S) | 48 |
| 47 | CLPDO-S | (S) | 42 |
| 48 | CLPF-R | (R) | 51 |

Examples 49 to 62

Preparation of 8-acetamidoalanine Esters Using Rhodium Metal Complex Catalyst

Each substrate for reduction (1.0 mmol) and each metal complex (0.005 mmol) were weighed in a Pyrex (registered trade name) test tube for autoclaving, the tube was set in a 50-mL autoclave together with a stirrer in the tube, and the atmosphere in the autoclave was substituted with nitrogen. The reaction mixture was added with 2 mL of methanol, the atmosphere in the autoclave was sufficiently substituted with hydrogen, and then pressurized with 2 MPa of hydrogen, and the reaction was allowed at 45° C. for 17 hours. After the reaction, the reaction mixture was added with 0.02 g of activated carbon, and stirred for 30 minutes, and after the activated carbon was removed, the reaction mixture was concentrated in an evaporator to quantitatively obtain each β-acetamidoalanine ester.

The resulting β-acetamidoalanine ester in an amount of 2 mg was dissolved in 1 mL of methanol, and analyzed by GC or HPLC under the following conditions.

3-Acetylaminobutanoic acid ethyl ester (R=Me, R'=Et)

Analysis conditions: column produced by SPELCO, β-DEX 325, column temperature: 140° C., injection temperature: 220° C., detector temperature: 300° C., mobile phase: 50 kPa of helium, split ratio: 50:1, FID detector, injection: 5 μL, R.T.: S-isomer=25.5 min., R-isomer=26.4 min.

$^1$H NMR (300 MHz, CDCl$_3$): δ 6.15 (brs, 1H), 4.39-4.31 (m, 1H), 4.21 (q, 7.2 Hz, 2H), 2.52 (dd, 2.8, 5.3 Hz, 2H), 1.96 (s, 3H), 1.27 (t, J=7.2 Hz, 3H), 1.23 (d, J=6.6 Hz, 3H)

3-Acetylaminopentanoic acid methyl ester (R=Et, R'=Me)

Analysis conditions: column produced by SPELCO, β-DEX 325, column temperature: 120° C., injection temperature: 220° C., detector temperature: 300° C., mobile phase: 50 kPa of helium, split ratio: 50:1, FID detector, injection: 5 μL, R.T.: S-isomer=54.4 min., R-isomer=56.0 min.

$^1$H NMR (300 MHz, CDCl$_3$): δ 6.09 (brs, 1H), 4.19-4.12 (m, 1H), 3.69 (s, 3H), 2.54 (dd, J=3.8, 5.0 Hz, 2H), 1.99 (s, 3H), 1.62-1.51 (m, 2H), 0.92 (t, J=7.5 Hz, 3H)

3-Acetylaminohexanoic acid ethyl ester (R=n-Pr, R'=Et)

Analysis conditions: Chiralcel OC produced by Daicel Chemical Industries, Ltd., n-hexane/2-propanol=9/1, 0.5 mL/min., 210 nm, 30° C., R.T.: S-isomer=25.4 min., R-isomer=30.0 min.

$^1$H NMR (300 MHz, CDCl$_3$): δ 6.09 (d, J=7.8 Hz, 1H), 4.30-4.19 (m, 1H), 4.15 (q, J=7.2 Hz, 2H), 2.52 (ddd, J=5.1, 15.8, 23.5 Hz, 2H), 1.97 (s, 3H), 1.61-1.29 (m, 4H), 1.25 (t, J=6.8 Hz, 3H), 0.91 (t, J=7.4 Hz, 3H)

3-Acetylamino-3-phenylpropanoic acid ethyl ester (R=Ph, R'=Et)

Analysis conditions: Chiralcel OD by Daicel Chemical Industries, Ltd., n-hexane/2-propanol=95/5, 1.0 mL/min., 220 nm, 40° C., R.T.: R-isomer=22.5 min., S-isomer=26.0 min.

$^1$H NMR (300 MHz, CDCl$_3$): δ 7.36-7.23 (m, 5H), 6.62 (d, J=7.8 Hz, 1H), 5.46-5.40 (m, 1H), 4.06 (q, J=7.8 Hz, 2H), 2.96-2.78 (m, 2H), 2.03 (s, 3H), 1.16 (t, J=7.2 Hz, 3H)

TABLE 8

| Example | Metal complex catalyst | R | R' | E/Z | Steric configuration | % ee |
|---|---|---|---|---|---|---|
| 49 | [Rh(CLPL-S)(COD)]BF$_4$ | Me | Et | Z | (R) | 24 |
| 50 | [Rh(CLPDO-S)(COD)]BF$_4$ | Me | Et | Z | (S) | 47 |
| 51 | [Rh(CLPL-S)(COD)]BF$_4$ | Me | Et | E | (S) | 66 |
| 52 | [Rh(CLPDO-S)(COD)]BF$_4$ | Me | Et | E | (S) | 89 |
| 53 | [Rh(CLPL-S)(COD)]BF$_4$ | n-Pr | Et | Z | (S) | 74 |
| 54 | [Rh(CLPDO-S)(COD)]BF$_4$ | n-Pr | Et | Z | (S) | 22 |
| 55 | [Rh(CLPL-S)(COD)]BF$_4$ | n-Pr | Et | E | (S) | 69 |
| 56 | [Rh(CLPDO-S)(COD)]BF$_4$ | n-Pr | Et | E | (S) | 94 |
| 57 | [Rh(CLPL-S)(COD)]BF$_4$ | Et | Me | Z | (S) | 6 |
| 58 | [Rh(CLPDO-S)(COD)]BF$_4$ | Et | Me | Z | (S) | 57 |
| 59 | [Rh(CLPL-S)(COD)]BF$_4$ | Et | Me | E | (S) | 76 |
| 60 | [Rh(CLPDO-S)(COD)]BF$_4$ | Et | Me | E | (S) | 95 |
| 61 | [Rh(CLPL-S)(COD)]BF$_4$ | Ph | Et | Z | (R) | 27 |
| 62 | [Rh(CLPDO-S)(COD)]BF$_4$ | Ph | Et | Z | (R) | 66 |

Me: methyl group,
Et: ethyl group,
n-Pr: n-propyl group,
Ph: phenyl group

Example 63

Preparation of [Ir(COD)(CLPDO-S)]BF$_4$

The preparation of the iridium metal complex was performed in the same manner as that of Example 16. To a 10 mL-recovery flask were added [IrCl(COD)]$_2$ (86.7 mg, 0.13 mmol) and silver tetrafluoroborate (52.7 mg, 0.26 mmol), and the atmosphere in the flask was substituted with nitrogen. The mixture was added with 2 mL of degassed ethanol, stirred for 10 minutes, and then filtered, and the residue was washed with 2 mL of ethanol. The filtrate and the wash were combined, added to a 25 mL-recovery flask containing CLPDO-S (0.13 g, 0.26 mmol) under a nitrogen atmosphere, and the mixture was stirred for 10 minutes. The reaction mixture was evaporated under reduced pressure until the remaining volume became about 1 mL, the remaining reaction mixture was added with 20 mL of diethyl ether, and the precipitated solid was collected by filtration and dried to obtain the title compound as reddish orange solid (0.22 g, yield: 94%).

Examples 64 to 66

Preparation of N-benzyl-1-phenylethylamine Using Rhodium or Iridium Metal Complex Catalyst

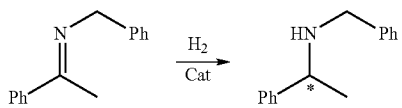

N-Benzyl-1-phenylethanimine (0.11 g, 0.5 mmol) and each metal complex (0.005 mmol) were weighed in a Pyrex (registered trade name) test tube for autoclaving, the tube was set in a 50-mL autoclave together with a stirrer in the tube, and the atmosphere in the autoclave was substituted with nitrogen. The mixture was added with 2 mL of methanol and Et$_3$N (14 μL, 0.1 mmol), the atmosphere in the autoclave was sufficiently substituted with hydrogen, and then pressurized with 5.0 MPa of hydrogen, and the reaction was allowed at 40° C. for 24 hours. After the reaction, the reaction mixture was added with 0.02 g of activated carbon and stirred for 30 minutes, and after the activated carbon was removed, the reaction mixture was concentrated in an evaporator to quantitatively obtain optically active N-benzyl-1-phenylethylamine.

$^1$H NMR (300 MHz, CDCl$_3$): δ 7.35-7.21 (m, 10H), 3.81 (q, 6.6 Hz, 1H), 3.63 (dd, J=7.2, 21.9 Hz, 2H), 1.37 (d, J=6.6 Hz, 3H)

The resulting N-benzyl-1-phenylethylamine was analyzed by HPLC under the following conditions.

Analysis conditions: Chiralcel-OJ produced by Daicel Chemical Industries, Ltd., mobile phase: n-hexane: 2-propanol:diethylamine=200:1:0.1, flow rate: 0.7 mL/min., detector wavelength: 220 nm, column temperature: 40° C., injection: 2 μL, R.T.: S-isomer=13.5 min., R-isomer=14.9 min.

TABLE 9

| Example | Metal complex catalyst | Steric configuration | % ee |
|---------|------------------------|----------------------|------|
| 64 | [Rh(CLPL-S)(COD)]BF$_4$ | (R) | 11 |
| 65 | [Rh(CLPDO-S)(COD)]BF$_4$ | (R) | 29 |
| 66 | [Ir(CLPDO-S)(COD)]BF$_4$ | (S) | 23 |

What is claimed is:

1. A compound represented by the following general formula (I):

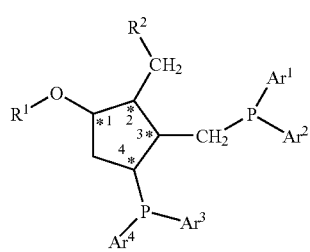

wherein
  R$^1$ represents a hydrogen atom or an alkyl group,
  R$^2$ represents a hydroxyalkyl group or a triarylmethyloxyalkyl group, or
  R$^1$ and R$^2$ combine together to represent —C(R$^3$)(R$^4$)—, wherein
    R$^3$ and R$^4$ independently represent a hydrogen atom, an alkyl group, or a hydroxyl group, or
    R$^3$ and R$^4$ may combine together to represent an oxo group, or R$^1$ and R$^2$ combine together to represent —C(R$^5$)(R$^6$)—O—C(R$^7$)(R$^8$)—, wherein
      R$^5$, R$^6$, R$^7$ and R$^8$ independently represent a hydrogen atom, an alkyl group, or a hydroxyl group, or
      R$^5$ and R$^6$ may combine together to represent an oxo group, and/or
      R$^7$ and R$^8$ may combine together to represent an oxo group; and
wherein
  Ar$^1$, Ar$^2$, Ar$^3$ Ar$^4$ independently represent aryl group, which may have 1 to 5 of the same or different substituents, and wherein
  *1, *2, *3 and *4 indicate asymmetric carbons, and relative steric configurations thereof are in cis-configuration between *1 and *2, cis-configuration between *3 and *4, and trans-configuration between *2 and *3.

2. The compound according to claim 1, wherein Ar$^1$, Ar$^2$, Ar$^3$ and Ar$^4$ independently represent a phenyl group, which may have 1 to 5 of the same or different substituents.

3. The compound according to claim 1, wherein Ar$^1$, Ar$^2$, Ar$^3$ and Ar$^4$ independently represent a phenyl group, or a 3,5-dialkyl-4-alkoxyphenyl group.

4. The compound according to claim 1, wherein R$^1$ is a hydrogen atom, and R$^2$ is a hydroxyalkyl group.

5. The compound according to claim 1, wherein R$^1$ is a hydrogen atom; or an alkyl group, and R$^2$ is a triphenylmethyloxyalkyl group.

6. The compound according to claim 1, wherein R$^1$ and R$^2$ combine together to represent —C(R$^3$)(R$^4$)—, wherein R$^3$ and R$^4$ both represent a hydrogen atom, or R$^3$ and R$^4$ combine together to represent an oxo group.

7. The compound according to claim 1, wherein R$^1$ and R$^2$ combine together to represent —C(R$^5$)(R$^6$)—O—C(R$^7$)(R$^8$)—, wherein R$^5$ and R$^6$ independently represent an alkyl group, and both R$^7$ and R$^8$ are hydrogen atoms.

8. The compound according to claim 1 and a transition metal, which together form a transition metal complex.

9. The transition metal complex according to claim 8, wherein the transition metal is selected from rhodium, ruthenium, iridium, and palladium.

10. A catalyst for an asymmetric reaction, which comprises the transition metal complex according to claim 9.

11. The catalyst according to claim 10, which is used for an asymmetric hydrogenation reaction of an olefin, an imine, or a ketone, or an asymmetric 1,4-addition reaction of an enone.

12. A phosphine borane compound consisting of the compound according to claim 1 having boranes added on each of the two phosphorus atoms of the compound.

13. A method for preparing the compound according to claim 1 comprising:
  having boranes added on each of the two phosphorus atoms of the compound and
  treating a phosphine borane compound, consisting of the compound according to claim 1 having boranes added on each of the two phosphorus atoms of the compound, with a base.

* * * * *